US012642868B2

(12) United States Patent
De Smedt et al.

(10) Patent No.: US 12,642,868 B2
(45) Date of Patent: Jun. 2, 2026

(54) THERAPEUTIC NANOPARTICLES AND METHODS OF USE THEREOF

(71) Applicant: Universiteit Gent, Ghent (BE)

(72) Inventors: Stefaan De Smedt, Mariakerke (BE); Rein Verbeke, Bruges (BE); Heleen Dewitte, Gentbrugge (BE); Ine Lentacker, Ledeberg (BE)

(73) Assignee: UNIVERSITEIT GENT, Ghent (BE)

( * ) Notice: Subject to any disclaimer, the term of this patent is extended or adjusted under 35 U.S.C. 154(b) by 1235 days.

(21) Appl. No.: 17/277,055

(22) PCT Filed: Sep. 17, 2019

(86) PCT No.: PCT/EP2019/074796
§ 371 (c)(1),
(2) Date: Mar. 17, 2021

(87) PCT Pub. No.: WO2020/058239
PCT Pub. Date: Mar. 26, 2020

(65) Prior Publication Data
US 2021/0369862 A1 Dec. 2, 2021

(30) Foreign Application Priority Data

Sep. 18, 2018 (EP) ..................................... 18195181
Apr. 12, 2019 (EP) ..................................... 19168853

(51) Int. Cl.
| | |
|---|---|
| *A61K 47/69* | (2017.01) |
| *A61K 31/7105* | (2006.01) |
| *A61K 39/00* | (2006.01) |
| *A61K 45/06* | (2006.01) |
| *A61K 47/54* | (2017.01) |
| *A61K 48/00* | (2006.01) |
| *A61P 35/00* | (2006.01) |
| *B82Y 5/00* | (2011.01) |

(52) U.S. Cl.
CPC ...... *A61K 47/6935* (2017.08); *A61K 31/7105* (2013.01); *A61K 39/00* (2013.01); *A61K 39/0011* (2013.01); *A61K 45/06* (2013.01); *A61K 47/543* (2017.08); *A61K 47/549* (2017.08); *A61K 48/0025* (2013.01); *A61P 35/00* (2018.01); *A61K 2039/5154* (2013.01); *A61K 2039/53* (2013.01); *A61K 2039/585* (2013.01); *B82Y 5/00* (2013.01)

(58) Field of Classification Search
CPC ............ A61K 47/6935; A61K 31/7105; A61K 39/0011; A61K 45/06; A61K 47/543; A61K 47/549; A61K 48/0025; A61K 2039/53; A61K 2039/585; A61K 39/00; A61K 2039/505; A61K 9/1272; A61K 9/5123; A61K 2039/5154; A61K 2039/55555; A61K 2039/55572; A61K 2039/804; A61K 39/0005; A61K 2039/572; A61K 2039/876; A61K 39/39; A61K 39/395; A61K 9/127; A61P 35/00; A61P 37/04; B82Y 5/00; C07K 16/2827; C07K 2317/76; C07K 16/28
See application file for complete search history.

(56) References Cited

U.S. PATENT DOCUMENTS

| | | | |
|---|---|---|---|
| 2011/0229556 A1 | 9/2011 | Irvine et al. | |
| 2012/0021050 A1* | 1/2012 | Zhou ...................... | A61K 39/39 |
| | | | 424/490 |
| 2015/0110875 A1* | 4/2015 | Linder ............... | A61K 47/6929 |
| | | | 514/777 |
| 2017/0042824 A1* | 2/2017 | Reinhard ............. | A61K 9/1271 |

FOREIGN PATENT DOCUMENTS

| | | | |
|---|---|---|---|
| WO | 2012031043 A1 | 3/2012 | |
| WO | 2012088414 A1 | 6/2012 | |
| WO | 2013143555 A1 | 10/2013 | |
| WO | 2014128225 A1 | 8/2014 | |
| WO | 2016154544 A1 | 9/2016 | |
| WO | WO-2018078053 A1 * | 5/2018 ............. | A61K 31/16 |

OTHER PUBLICATIONS

Thapa et al. Nanoparticle formulated alpha-galactosylceramide activates NKT cells without inducing anergy. Vaccine. May 26, 2009;27(25-26):3484-8. (Year: 2009).*
Fuji et al. NKT cells as an ideal anti-tumor immunotherapeutic. Front Immunol. Dec. 2, 2013:4:409. (Year: 2013).*
Derived. Dictionary.com (accessed at https://www.dictionary.com/browse/derived on Aug. 1, 2024) (Year: 2023).*
Li et al. Design of a potent CD1 d-binding NKT cell ligand as a vaccine adjuvant. Proc Natl Acad Sci U S A. Jul. 20, 2010;107(29):13010-5. Epub Jul. 2, 2010. (Year: 2012).*
Bhattacharya et al. Understanding Membranes through the Molecular Design of Lipids. Langmuir. Apr. 6, 2010;26(7):4642-54. (Year: 2010).*
Mizrahy et al. Advanced strategies in immune Modulation of cancer Using Lipid-Based Nanoparticles. Front Immunol. Feb. 6, 2017:8:69. (Year: 2017).*
Matthew B. Bloom et al., The Journal of Experimental Medicine, vol. 185, No. 3, Feb. 3, 1997 453459.
E. Jonasch, et al., "Interferon in Oncological Practice: Review of Interferon Biology, Clinical Applications, and Toxicities," The Oncologist, 6 (2001), pp. 34-55.

(Continued)

*Primary Examiner* — Valarie E Bertoglio
*Assistant Examiner* — Briana N Ebbinghaus
(74) *Attorney, Agent, or Firm* — DINSMORE & SHOHL LLP

(57) ABSTRACT

The present invention relates to a method and composition for optimized intracellular delivery of nucleic acids, in particular mRNA. In addition to mRNA, the composition, in particular a nanoparticle, may include a glycolipid antigen. Combinations with checkpoint inhibitors are also provided. The method and composition of the invention targets antigen presenting cells and is especially useful for immunotherapy and vaccination purposes.

11 Claims, 20 Drawing Sheets

(56)            References Cited

OTHER PUBLICATIONS

S. Van Meirvenne, et al., Cancer Gene Therapy, 9 (2002), pp. 787-797.

S. Fujii, et al., The Journal of Experimental Medicine, 198 (2003), pp. 267-279.

A.N. Theofilopoulos, et al., "Type I Interferons (a/B) in Immunity and Autoimmunity," Annual Review of Immunology, 23 (2005), pp. 307-336.

K. Kariko, et a., "Suppression of RNA Recognition by Toll-like Receptors: The Impact of Nucleoside Modification and the Evolutionary Origin of RNA," Immunity, 23 (2005), pp. 165-175.

K. Kariko, et al., "Incorporation of Pseudouridine Into MRNA Yields Superior Nonimmunogenic Vector With Increased Translational Capacity and Biological Stability," Molecular Therapy: The Journal of the American Society of Gene Therapy, 16 (2008), pp. 1833-1840.

J. Wang, et al., The Journal of Immunology, 182 (2009), pp. 6644-6647.

V.V. Parekh, et al., Journal of Immunology, 182 (2009), pp. 2816-2826.

Akinc A, et al., Mol. Ther. Jul. 2010;18(7):1357-64.

B.R. Anderson, et al., " Incorporation of pseudouridine into mRNA enhances translation by diminishing PKR activation," Nucleic Acids Research, 38 (2010), pp. 5884-5892.

K. Braeckmans, et al., Nano Letters, 10 (2010), pp. 4435-4442.

M. Diken, et al., Gene Ther., 18 (2011), pp. 702-708.

U. Sahin, et al., "mRNA-based therapeutics developing a new class of drugs," Nature Reviews, Drug Discovery, 13 (2014), pp. 759-780.

G. Wingender, et al., J. Immunol., 195 (2015), pp. 3838-3848.

J. Crouse, et al., "Regulation of antiviral T cell responses by type I interferons," Nature Reviews, Immunology, 15 (2015), pp. 231-242.

J. Devoldere, et al., "Evading innate immunity in nonviral mRNA delivery: don't shoot the messenger," Drug Discovery Today, (2015).

O. Andries, et al., "N1-methylpseudouridine-incorporated mRNA outperforms pseudouridine-incorporated mRNA by providing enhanced protein expression and reduced immunogenicity in mammalian cell lines and mice," J. Control Release, 217 (2015), pp. 337-344.

A. De Beuckelaer, et al., Molecular Therapy: The Journal of the American Society of Gene Therapy, 24 2016), pp. 2012-2020.

L.M. Kranz, et al., "Systemic RNA delivery to dendritic cells exploits antiviral defence for cancer immunotherapy," Nature, 534 (2016), pp. 396-401.

A. De Beuckelaer, et al. J. Grooten, S. De Koker, "Type I Interferons Modulate CD8+ T Cell Immunity to mRNA Vaccines," Trends in Molecular Medicine, 23 (2017), pp. 216-226.

A. Garcia-Diaz, et al., "Interferon Receptor Singaling Pathways Regulating PD-L1 and PD-L2 Expression," Cell Reports, 19 (2017), pp. 1189-1201.

C. Lavarone, et al., "Mechanism of action of mRNA-based vaccines," J.B. Ulmer, Expert Rev Vaccines, 16 (2017), pp. 871-881.

F. Liang, et al., "Efficient Targeting and Activation of Antigen-Presenting Cells In Vivo after Modified mRNA Vaccine Administration in Rhesus Macaques," Molecular Therapy: The Journal of the American Society of Gene Therapy, 25 (2017), pp. 2635-2647.

Ghinnagow, et al.; "Enhancement of Adjuvant Functions of Natural Killer T Cells Using Nanovector Delivery Systems: Application in Anticancer Immune Therapy;" Frontiers in Immunology; vol. 8; Jul. 27, 2017.

K.G. Anderson, et al., "Obstacles posed by the tumor microenvironment to T cell activity: a case for synergistic therapies," Cancer Cell, 31 (2017), pp. 311-325.

Kulkarni JA, et al., "Rapid synthesis of lipid nanoparticles containing hydrophobic inorganic nanoparticles, " Nanoscale, Sep. 21, 2017; 9(36):13600-13609.

M.A. Oberli, et al., "Lipid Nanoparticle Assisted mRNA Delivery for Potent Cancer Immunotherapy," Nano Letters, 17 (2017), pp. 1326-1335.

R. Verbeke, et al., "Co-delivery of nucleoside-modified mRNA and TLR agonists for cancer immunotherapy: Restoring the immunogencity of immunosilent mRNA," J. Control Release, 266 (2017), pp. 287-300.

T. Pepini, et al., "Induction of an IFN-Mediated Antiviral Response by a Self-Amplifying RNA Vaccine: Implications for Vaccine Design," The Journal of Immunology, (2017).

V.R. Juneja, et al., "PD-L1 on tumor cells is sufficient for immune evasion in immunogenic tumors and inhibits CD8 T cell cytotoxicity," The Journal of Experimental Medicine, 214 (2017), pp. 895-904.

C. Sun, et al., "Regulation and Function of the PD-L1 Checkpoint," Immunity, 48 (2018), pp. 434-452.

Kulkarni JA, et al., "On the Formation and Morphology of Lipid Nanoparticles Containing Ionizable Cationic Lipids and siRNA," ACS Nano., May 22, 2018;12(5):4787-4795.

N. Pardi, et al., "Nucleoside-modified mRNA vaccines induce potent T follicular helper and germinal center B cell responses," The Journal of Experimental Medicine, 215 (2018), pp. 1571-1588.

Rein Verbeke, et al.; "Broadening the Message: A Nanovaccine Co-loaded with messenger RNA and [alpha]- GalCer Induces Antitumor Immunity through Conventional and Natural Killer T Cells;" ACS Nano; Feb. 11, 2019.

International Search Report and Written Opinion dated Sep. 17, 2019 in related International Application No. PCT/EP2019/074796.

Neumann, et al., "Synthetic TRP2 long-peptide and α-galactosylceramide formulated into cationic liposomes elicit CD8+ T-cell responses and prevent tumour progression", Vaccine, vol. 33, pp. 5838-5844, 2015.

Pardi, et al., "mRNA vaccines—a new era in vaccinology", Nature Reviews, vol. 17, pp. 1-19, Apr. 2018.

Sahin, et al., "Personlized RNA mutanome vaccines mobilize poly-specific therapeutic community against cancer", Nature reviews, vol. 547, pp. 1-19, Jul. 13, 2017.

* cited by examiner

Tumor growth curve E.G7-OVA

Tumor-infiltrating effector cells

A

CTLs
(CD3+, CD8+)

***

B

OVA specific CTLs
(CD3+, CD8+, OVA tetr+)

****

C

NKT cells
(TCRb+, CD1d tetr+)

**

D

NK cells
(CD3-, NK1.1+)

*    **

THERAPEUTIC NANOPARTICLES AND METHODS OF USE THEREOF

CROSS-REFERENCE TO RELATED APPLICATIONS

This application is a national stage application under 35 U.S.C. § 371 of International Application No. PCT/EP2019/074796, filed Sep. 17, 2019, which claims the benefit of EP 19168853.0, filed Apr. 12, 2019 and EP 18195181.5, filed Sep. 18, 2018, each of which is incorporated herein by reference in its entirety.

FIELD OF THE INVENTION

The present invention relates to a method and composition for optimized intracellular delivery of nucleic acids, in particular mRNA. In addition to mRNA, the composition, in particular a nanoparticle, may include a glycolipid antigen. Combinations with checkpoint inhibitors are also provided. The method and composition of the invention targets antigen presenting cells and is especially useful for immunotherapy and vaccination purposes.

BACKGROUND TO THE INVENTION

Where for long the use of messenger RNA was limited due to its perceived instability, it is nowadays possible to successfully deliver mRNA in vivo [1]. This is strongly supported by two recent breakthroughs in this field: (i) the packaging of mRNA molecules inside nanoparticles, designed to improve the selective cell targeting and cytosolic delivery of mRNA [2, 3] and (ii) the technical progress in the mRNA construct, including the incorporation of modified nucleotides, yielding more stable mRNA with improved translation capacity [4-7]. Particularly in the field of vaccination, mRNA encoded antigens have emerged as a versatile and promising platform [8].

In the field of cancer immunotherapy, Kranz et al. provided first-in-human proof that by targeting mRNA lipid nanoparticles to dendritic cells (DCs), cytotoxic T cell (CTL) responses were induced against the encoded tumor antigens [2]. They and others demonstrated that besides the successful mRNA expression by dendritic cells, the mode of action of mRNA vaccines depends on the induction of type I interferons (IFN) [3, 9, 10]. More specifically, upon cell entry mRNA molecules trigger innate immune activation pathways, including the endosomal Toll-like receptor (TLR)-7 and cytosolic receptors MDA-5 and RIG-1, which results in type I IFN signaling and the induction of antiviral immunity. In prior art, mRNA vaccines rely on this inherent self-adjuvant effect of mRNA. However these vaccines hold important limitations, as it was shown that type I IFN signaling acts as a double-edged sword as the evoked immune response prematurely stops mRNA-translation, thereby lowering antigen bioavailability [11, 12]. Moreover, it was suggested that type I IFNs, depending on the relative timing to T cell priming, can either positively or negatively affect T cell responses, with pre-exposure of type I IFNs resulting in T cell exhaustion and apoptosis [13, 14]. In addition, high levels of IFNα can induce adverse effects ranging from flu-like symptoms to autoimmune sequelae and even life-threatening events [15, 16].

Several modifications of the mRNA construct or additional purification steps, including the removal of double stranded RNA fragments by HPLC, have potential to down-modulate the immune stimulatory aspect of mRNA molecules, provoking reduced type I IFN levels. For instance, the incorporation of modified nucleotides (e.g. pseudouridine (Ψ), N1-methylpseudouridine (m1Ψ) and 5-methylcytidine (5meC) improves the mRNA stability and translation, resulting in higher and more sustainable levels of mRNA expression. This enhanced mRNA expression is advantageous in the development of vaccines, since the resulting increased antigen presentation is shown to be beneficial for the induction of long-lived antibody and helper T cell responses, including the formation of follicular T cells [17]. However, nucleoside-modified mRNA largely loses its self-adjuvancy, resulting in reduced type I IFN levels, and a limited capacity to evoke CTL immunity.

Prior research has shown a lipid nanoparticle in which both nucleoside-modified mRNA and monophosphoryl lipid A (MPLA) can be encapsulated, achieving a restored capacity to obtain T cell numbers without the strong induction of type I IFNs [18]. However, this combination strategy of nucleoside-modified mRNA and MPLA did not had significant effects on tumor growth, underlining the involvement of type I IFN in multiple antitumor mechanisms (e.g. activation of NK cells, reduction of regulatory T cells).

The use of adjuvants has also been shown in peptide and protein based cancer vaccines using nanoparticles (e.g. WO2012/088414, WO2016/154544, WO2014/128225, US2011229556). Findings from protein or protein-nanoparticle vaccines are only helpful to a certain extent, because intracellular location of the antigen, antigen processing and presentation is completely different for mRNA vaccines. Previous attempts where mRNA was combined with other adjuvants (e.g. Poly(I:C) and lipopolysaccharide) have raised compatibility issues, since DC maturation can prematurely abrogate cellular uptake mechanisms (e.g. macropinocytosis), as well as create an unfavorable environment for mRNA translation [2, 19]. There is still an important need to identify appropriate and safe immune stimulants that can be combined with nucleoside-modified mRNA vaccines, in order to modulate their immunogenicity, achieving strong and durable CTL responses.

Besides issues related to vaccine-induced type I IFN secretion, mRNA vaccines often fall short to evoke durable antitumor immunity. In essence, tumor-infiltrating CTLs have to deal with immune resistance mediated by various suppressive cells, including M2 macrophages, myeloid derived suppressor cells (MDSCs) and regulatory T cells [20]. Additionally, during immune attack and the production of interferons, immune checkpoint pathways are activated as mechanisms to resist adaptive immunity, such as the expression of programmed cell death 1 (PD-1) ligand by tumor cells, antigen presenting cells (APCs) and its receptor PD-1 on the effector cells [21-23]. Thus, ideally, mRNA vaccines should not solely focus on the activation of CTLs, but should more broadly harness the host's immune system to tackle these different suppressive mechanisms.

SUMMARY OF THE INVENTION

The present invention relates to nanoparticles associated (e.g., complexed, conjugated, encapsulated, absorbed, adsorbed, admixed) with nucleic acids configured for treating, preventing or ameliorating various types of disorders, methods of using said nanoparticles and a method of synthesizing the same. In addition, the invention provides a method, compositions, kits, combinations and uses thereof, for optimized cytosolic delivery of nucleic acids. The composition, kit or combination comprises a nanoparticle, a nucleic acid, in particular mRNA, and at least one adjuvant, in particular an iNKT agonist. The composition optionally comprises a pharmaceutically acceptable excipient or diluent.

In one embodiment, the nanoparticle is a lipid-based nanoparticle and/or a cationic nanoparticle, in particular a cationic liposome, which is associated with or comprises a nucleic acid. In a further embodiment, the lipid component of the nanoparticle comprises a lipid, more specific a cationic lipid (such as e.g. DOTAP) or an ionizable lipid, and a helper lipid(s), such as e.g. a phospholipid, cholesterol or (functional) derivative or analog thereof, and/or PEG. The nanoparticle is further associated with an adjuvant, in particular an immunity stimulating adjuvant, more in particular an iNKT agonist. More particular, the nanoparticle of the invention comprises mRNA, a lipid component and α-Gal-Cer or analogs thereof. mRNA includes the partly or complete incorporation of modified nucleosides such as pseudouridine (IP), N1-methylpseudouridine (m1Ψ) and/or 5-methylcytidine (5meC) into the mRNA transcript.

In one embodiment the α-GalCer compound is incorporated in the lipid component of the nanoparticle. The concentration of the α-GalCer compound in the nanoparticle is between and about 0.0015 mol % and about 1 mol % of the total lipid amount (<1 µg/kg body weight). The concentration of cholesterol in the nanoparticle is between 40 mol % and 80 mol % of the total lipid amount. The concentration of DOTAP in the nanoparticle is between 20 mol % and 60 mol % of the total lipid amount.

The mRNA as provided herein encodes an antigen or polypeptide of interest, in particular a tumor specific antigen. Optionally, said mRNA includes a chain terminating nucleoside, a polyA sequence, a polyadenylation signal, and/or a 5' cap structure.

In one embodiment, the wt/wt ratio of the lipid component to the mRNA in the nanoparticle is from about 5:1 to about 50:1.

In a further embodiment, the nanoparticle, the composition, kit or combination of the present invention is used as a medicament, in particular in a method of delivering an agent into the cytosol of a dendritic cell by in vitro, ex vivo or in vivo application, more in particular for use in treating cancer, infectious diseases or auto-immune diseases.

More specific, the invention provides a method for delivering and/or expressing an antigen to antigen-presenting cells, preferably antigen-presenting cells in the spleen and lungs, said method comprising administering the nanoparticle or composition as provided herein. In a particular embodiment, the antigen-presenting cells are dendritic cells or macrophages.

In a further embodiment, the invention provides a nanoparticle or composition for use in a method for inducing an immune response, preferably an immune response against cancer, in a subject, comprising administering to the subject the nanoparticle or composition as described herein. The nanoparticle or composition is able to stimulate, prime and/or expand cytotoxic T cells and/or iNKT cells in a subject.

The invention further provides a method of inducing expression of an antigen in a cell and of inducing an antigen-specific T cell immune response, comprising administering a composition comprising:

(a) at least one nucleoside-modified mRNA at least a portion of which encodes the antigen; and (b) a glycolipid antigen, which presented in CD1d molecules, stimulate iNKT cells; and (c) a lipid nanoparticle comprising nucleoside-modified mRNA; and

(d) optionally a PD-1 or PD-L1 inhibitor or other checkpoint inhibitor provided herein or known to the skilled person, wherein following administration of said composition, the antigen encoded by the mRNA is expressed in the target cell, and/or is secreted or excreted from the cell, and the glycolipid antigen is presented in the CD1d pathway by the same target cell.

The glycolipid recognition by iNKT cell evokes an immune cascade, characterized by production of IFN-γ and IL-12p70, which results in the priming and/or expansion of cytotoxic T cells and/or iNKT cells and/or NK cells in a subject.

In one embodiment, the nanoparticle or composition of the invention is administered in two, three or more (subsequent) doses to the subject, e.g. two times a week, at least once a week, or every two weeks. Administration can be intravenous, intradermal, subcutaneous, intraperitoneal, intratracheal, intranasal or via inhalation.

In a specific aspect, the polypeptide of interest is expressed or produced in a mammalian cell. In yet another aspect, the invention provides a method of delivering an mRNA to a cell (e.g., a mammalian cell) involving administering to a subject (e.g., a mammal) a nanoparticle composition including (i) a lipid component, (ii) a mRNA and (iii) an iNKT cell agonist, in which administering involves contacting the cell with the nanoparticle composition, whereby the mRNA and glycolipid antigen are delivered to the cell.

Of particular interest is the combination and the combined use (in the methods of the invention; first and further medical use) of the nanoparticle or composition provided herein with a PD-1 or PD-L1 inhibitor or other checkpoint inhibitor (e.g. anti-CTLA4, anti-PD-L2, . . . ), such as an antibody, a small molecule, a polypeptide or a nucleic acid, and in particular an anti-PD-1 or anti-PD-L1 antibody. The combination is particular useful in treating cancer, infectious diseases or auto-immune diseases.

The invention further encompasses a kit which comprises a first container, a second container and a package insert, wherein the first container comprises at least one dose of a pharmaceutical composition containing the nanoparticle provided herein, the second container comprises at least one dose of a pharmaceutical composition comprising a checkpoint inhibitor as described herein, and the package insert comprises instructions for treating an individual having e.g. cancer, an infectious disease or an autoimmune disease using the pharmaceutical composition(s).

BRIEF DESCRIPTION OF THE DRAWINGS

With specific reference to the figures, it is to be noted that the particulars shown are by way of example and for purposes of illustrative discussion of the different embodiments of the present invention. The description taken with the figures make it apparent to those skilled in the art how the several forms of the invention may be embodied in practice.

DETAILED DESCRIPTION OF THE INVENTION

Figure 1:
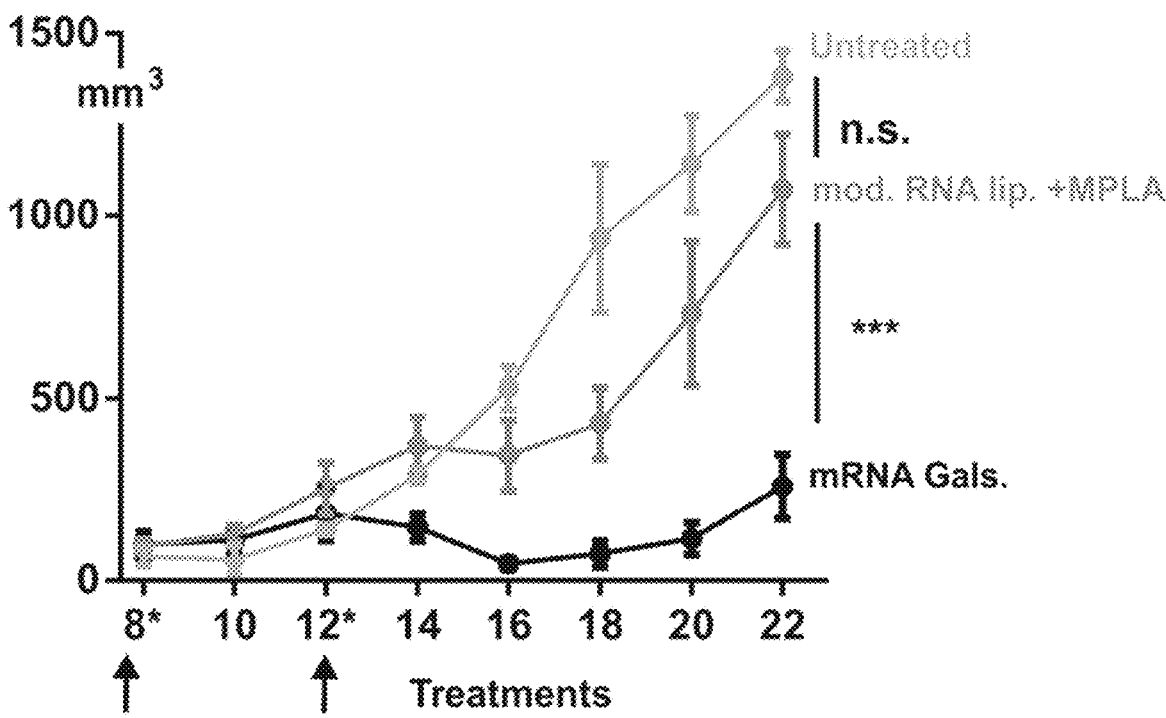
FIG. 1. Therapeutic efficacy in E.G7-OVA tumor bearing mice after systemic administration of (i) OVA-encoded nucleoside-modified nanoparticles containing low doses of α-GalCer (~0.020 µg α-GalCer per mouse) versus (ii) mRNA nanoparticles adjuvanted with MPLA (~2 µg MPLA per mouse). Mice were subcutaneously inoculated with E.G7-OVA lymphoma cells (3×10⁵ cells). E.G7-OVA tumor bearing mice were intravenously administered with mRNA nanoparticles on day 8 (when tumors were clearly visible) and received a second vaccination on day 12 after tumor inoculation (n=6).

The present invention will now be further described. In the following passages, different aspects of the invention are defined in more detail. Each aspect so defined may be combined with any other aspect or aspects unless clearly indicated to the contrary. As used in the specification and the appended claims, the singular forms "a", "an", and "the" include plural referents unless the context clearly dictates otherwise. By way of example, "a compound" means one compound or more than one compound. Throughout the description and claims of this specification the word "comprise" and other forms of the word, such as "comprising" and "comprises," means including but not limited to, and is not intended to exclude, for example, other additives, components, integers, or steps. As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus 10% of the particular value or term. The terms described above and others used in the specification are well understood to those in the art. All references, and teachings specifically referred to, cited in the present specification are hereby incorporated by reference in their entirety.

The present invention relates to a mRNA delivery system targeting antigen presenting cells, inducing mRNA expression and evoking an appropriate immune response. It was surprisingly found that by incorporating only a low amount of an iNKT cell agonist into the lipid composition of the delivery system, an effective antigen-specific T cell immune response is generated together with a balanced cytokine response and iNKT/NK cell activation. In contrast to prior art, this platform allows that the mRNA construct can optimally be designed to obtain improved expression levels for antigen recognition.

We demonstrated herein that combining nucleoside-modified mRNA with the glycolipid α-galactosylceramide (α-GalCer), or a functional analog thereof, offers unique properties for (cancer) immunotherapy. More specifically, α-GalCer is a well-known glycolipid antigen that, when presented by antigen-presenting cells in the MHC-I-like molecule CD1d, leads to the potent activation of invariant natural killer T cells (iNKT). This subset of unconventional T cells contributes to innate and adaptive immunity, but can also exert direct and indirect antitumor effects. Unlike the classical immune adjuvants that directly trigger danger pathways, α-GalCer exerts an indirect adjuvant effect through the bidirectional interaction between α-GalCer-presenting DCs and iNKT cells. As such, iNKT cells can activate mRNA-transfected APCs through the interaction between CD40 and CD40 ligand, evoking the production of cytokines (e.g. IL-12p70, IFN-γ) and expression of co-stimulatory receptors (e.g. CD80, CD86, and CD70).

In the present invention, it was shown that the combination of nucleoside-modified mRNA with the iNKT ligand, such as e.g. an α-GalCer compound (incorporated at very low concentrations) not only promotes T cell immunity, but also offers the advantage of activating NKT- and NK cells shaping a broader and synergistic antitumor immunity.

In the present invention, the combination of nucleoside-modified mRNA with the iNKT ligand drastically alters disease-mediated immune-suppressive mechanisms. Essentially, the present invention reduced the number and functionality of MDSCs and macrophages with an immunosuppressive phenotype.

The present invention can induce a protective immune response which can be further strengthened by combination of the vaccine platform with state-of-the art immunotherapies (e.g. checkpoint inhibitors).

In one embodiment, the invention is directed to a nanoparticle comprising nucleoside-modified mRNA, a lipid composition and an iNKT-cell agonist, in particular a glycolipid antigen such as e.g. α-GalCer, or a functional analog or derivative thereof.

In one embodiment, the mRNA is incorporated in a nanoparticle, in particular a cationic nanoparticle. The term "nanoparticle" as used herein can be interpreted broadly and refers to a carrier being used as a transport module for another substance, such as a drug, in particular a nucleic acid, more in particular mRNA. Nanoparticles are currently being studied for their use in e.g. drug delivery and range from sizes of diameter 5-1000 nm, in particular from about 5 to about 500 nm, more in particular from about 50 to about 400 nm. In particular, the size of the nanoparticle is such that it is capable of being taken up by a mammalian cell, in particular an antigen presenting cell such as e.g. a dendritic cell. The term "cationic nanoparticle" refers to a nanoparticle comprising a cationic agent embedded in the core or at the surface. Where the nanoparticle is to be used for complexation of nucleic acids as a therapeutic agent, the positively charged nanoparticle is believed to interact electrostatically with the negatively charged DNA/RNA molecules, which not only facilitates complexation of the therapeutic, but which may also protect the latter from enzymatic degradation.

In one embodiment, the cationic agent may be a polycationic agent such as but not limited to chitosan, peptides (such as poly(L-lysine)), peptide derivatives (such as poly (L-lysine)-palmitic acid), polyethylenimine, poly(amido ethylenimine), and poly(amido amine)s. A particular polycationic agent is a polymer, preferably a polysaccharide, more preferably dextran, which is functionalized with a reactive (meth)acrylate moiety and subsequently co-polymerized with a cationic (meth)acrylate monomer such as 2-aminoethyl methacrylate, 2-(diethylamino)ethyl methacrylate, 2-(dimethylamino)ethyl methacrylate, 2-N-morpholinoethyl methacrylate, 2-(tert-butylamino)ethyl methacrylate, 2-(diisopropylamino)ethyl methacrylate, or [2-(methacryloyloxy)-ethyl] trimethylammonium chloride.

In a further embodiment, the nanoparticle of the invention is a carrier comprising a lipid component, also referred to as a lipoplex formulation or lipid-based nanoparticle, and including solid lipid nanoparticles, liposomes and micelles. The use of lipid-based nanoparticles to facilitate the delivery of nucleic acids, and especially mRNA, to target cells is especially contemplated by the present invention. Bilayer membranes of said nanoparticles are typically formed by amphiphilic molecules, such as lipids of synthetic or natural origin that comprise spatially separated hydrophilic and hydrophobic domains. Bilayer membranes of the (lipid) based nanoparticles can also be formed by amphiphilic polymers and surfactants (e.g., polymerosomes, niosomes, etc.). Examples of suitable lipids include, for example, the phosphatidyl compounds (e.g., phosphatidylglycerol, phosphatidylcholine, phosphatidylserine, phosphatidylethanolamine, sphingolipids, cerebrosides, and gangliosides).

In the context of the present invention, a lipid-based nanoparticle typically serves to transport the nucleic acid, such as e.g. the mRNA, to the target cell. The incorporated nucleic acids may be completely or partially located in the interior space of the particle, within the bilayer membrane of the particle, or associated with the exterior surface of the particle membrane. The association of a nucleic acid with a nanoparticle is also referred to herein as "encapsulation" wherein the nucleic acid is entirely integrated into the particle. The particle protects the nucleic acid from an environment which may contain enzymes or chemicals and allow the encapsulated nucleic acid to reach the target cell.

While the nanoparticle can facilitate introduction of nucleic acids into target cells, the addition of polycations as provided herein, as a copolymer can facilitate, and in some instances markedly enhance the transfection efficiency.

In a further embodiment, the lipid component is or comprises a cationic lipid, i.e. the lipid-based nanoparticles may be prepared by including multi-component lipid mixtures of varying ratios employing one or more cationic lipids, optionally in combination with non-cationic lipids and PEG-modified lipids. The cationic lipids are generally included to allow electrostatic complexation of the negatively charged DNA/RNA molecules, and can roughly be subdivided according to the pKa of the amino group into (i) "permanently-charged lipids", such as e.g. DOTMA, DOTAP and DC-cholesterol, or (ii) "pH-dependent ionizable lipids", such as e.g. D-Lin-MC3-DMA and the lipid-like molecule C12-200. The terms "cationic lipid" and "amino lipid" are used interchangeably herein to include those lipids and salts thereof having one, two, three, or more fatty acid or fatty alkyl chains and a pH-titratable amino head group (e.g., an alkylamino or dialkylamino head group). Several cationic lipids have been described in the literature, many of which are commercially available. Particularly suitable cationic lipids for use in the compositions and methods of the invention include 1,2-Dioleoyl-3-Trimethylammonium-Propane or "DOTAP", N-[1-(2,3-dioleyloxy)propyl]-N,N,N-trimethylammonium chloride or "DOTMA", 5-carboxyspermylglycinedioctadecylamide or "DOGS," 2,3-dioleyloxy-N-[2(spermine-carboxamido) ethyl]-N,N-dimethyl-l-propanaminium or "DOSPA", 1,2-Dioleoyl-3-Dimethylammonium-Propane or "DODAP". Ionizable lipids have a pKa<7 and have a neutral to mildly cationic charge under physiological pH conditions. Said ionizable cationic lipids with primary, secondary, or tertiary amines in the headgroup have been developed for the purposes of encapsulating nucleic acids when the lipid is positively charged at pH values below the pKa (e.g. pH 4), and for almost neutral LNP at physiological pH values. This offers certain benefits over the permanently-charged lipids, the foremost of which is that ionizable lipids have been associated with a reduced toxicity and a prolonged blood circulation lifetime. Contemplated cationic or "ionizable" cationic lipids also include 1,2-distearyloxy-N,N-dimethyl-3-aminopropane or "DSDMA", 1,2-dioleyloxy-N,N-dimethyl-3-aminopropane or "DODMA", 1,2-dilinoleyloxy-N, N-dimethyl-3-aminopropane or "DLin DMA", heptatriaconta-6,9,28,31-tetraen19-yl 4-(dimethylamino)butanoate or "DLin-MC3-DMA" or "MC3", 2,2-dilinoleyl-4-(2-dimethylaminoethyl)-[1,3]-dioxolane or "DLin-KC2-DMA" or "KC2", 1,2-dilinolenyloxy-N,N-dimethyl-3-aminopropane or "DLenDMA", N-dioleyl-N,N-dimethylammonium chloride or "DODAC", N,N-distearyl- N,N-dimethylammonium bromide or "DDAB", N-(1,2-dimyristyloxyprop-3-yl)-N,N-dimethyl-N-hydroxyethyl ammonium bromide or "DMRIE", 3-dimethylamino-2-(cholest-5-en-3-beta-oxybutan-4-oxy)-l-(cis, cis-9,12-octadecadienoxy)propane or "CLinDMA", 2-[5'-(cholest-5-en-3-beta-oxy)-3'-oxapentoxy)-3-dimethyl-1-(cis,cis-9',1-2'-octadecadienoxy)propane or "CpLinDMA", N,N-dimethyl-3,4-dioleyloxybenzylamine or "DMOBA", 1,2-N,N'-dioleylcarbamyl-3-dimethylaminopropane or "DOcarbDAP", 2,3-Dilinoleoyloxy-N,N-dimethylpropylamine or "DLinDAP", 1,2-N,N'-Dilinoleylcarbamyl-3-dimethylaminopropane or "DLincarbDAP", 1,2-Dilinoleoylcarbamyl-3-dimethylaminopropane or "DLinCDAP", 2,2-dilinoleyl-4-dimethylaminoethyl[1,3]-dioxolane or "DLin-K-XTC2-DMA.

The concentration of the cationic lipid in the nanoparticle is between 15 mol % and 65 mol %, in particular between 20 mol % and 60 mol %, and more in particular between 35 mol % and 45 mol % of the total lipid amount.

In a particular embodiment of the invention, the cationic lipid 1,2-dioleoyloxy-3-trimethylammonium propane or "DOTAP" is used in the carrier. DOTAP can be formulated alone or can optionally be combined with a neutral lipid or other cationic or non-cationic lipids into a liposomal transfer vehicle or a lipid nanoparticle, and such lipid-based nanoparticles can be used to enhance the delivery of nucleic acids into target cells. In a particular embodiment, the lipid component of the nanoparticle of the present invention does not comprise dioleoylphosphatidyl-ethanolamine (DOPE).

In a further embodiment, the nanoparticle as provided herein comprises cholesterol. More in particular, the lipid component of the nanoparticle comprises a combination of a lipid, in particular a cationic lipid, more in particular DOTAP, and cholesterol. Said particles have been shown in the present examples to be particularly stable in serum. The lipid component of the nanoparticle comprises between 40 mol % and 80 mol % cholesterol. In particular, the concentration of cholesterol in the nanoparticle is between 55 mol % and 65 mol % of total lipid amount.

The use of cholesterol-based cationic lipids is also contemplated by the present invention. Such cholesterol-based cationic lipids can be used, either alone or in combination with other cationic or non-cationic lipids as part of the lipid component of the nanoparticle. Suitable cholesterol-based cationic lipids include, for example, DC-Cholesterol 3beta-[N—(N',N'-dimethylaminoethane)-carbamoyl] cholesterol, 1,4-bis(3-N-oleylamino-propyl)piperazine or ICE. As an alternative to cholesterol, other structural lipids or analogs can be used, such as lipids selected from the group consisting of fecosterol, sitosterol, ergosterol, campersterol, stigmasterol, brassicasterol, tomatidine, ursolic acid and alpha-tocopherol.

The nanoparticle of the invention may be customized in terms of size, surface charge and attachment of any targeting moieties such as e.g. antibodies, peptides, folate, carbohydrates (such as mannose, galactose or GalNAc), haloperidol, anisamide, and cardiac glycosides or the like. Furthermore, the nanoparticle surface can be modified with poly(ethylene glycol) (PEG) or related polymers or moieties that are able to maintain nanoparticle colloidal stability, reduce nonspecific interactions and recognition by the immune system.

In general, the nanoparticle of the invention is suitable for use with genetic material as the (therapeutic) agent. The agent may be encapsulated by the nanoparticle or it may be attached to a surface or surfaces thereof to form a conjugate. Suitable methods for encapsulating agents inside nanoparticles are known to the skilled person and comprise electro-static complexation, covalent coupling, hydrophobic interactions, passive loading, remote loading, salting-out, nanoprecipitation, emulsion-diffusion, solvent-evaporation, spray drying and emulsion polymerization. Typically such methods may be adapted depending upon the materials used to make the nanoparticles and the chosen agent, which adaptation will be within the remit of the skilled person.

In a particular embodiment, the genetic material is a nucleic acid, including (plasmid) DNA, RNA, messenger RNA (mRNA), DNA antisense oligonucleotides, RNA antisense oligonucleotides, triplex forming oligonucleotides, transcription factor decoy oligonucleotides, small non-coding RNAs (e.g. siRNA, dsiRNA or miRNA) and long non-coding RNAs.

Particularly preferred are complexes of a nanoparticle and mRNA, and more specific mRNA nanoparticles. A mRNA may be a naturally or non-naturally occurring mRNA. A mRNA may include one or more modified nucleobases, nucleosides, or nucleotides. A nucleobase of a mRNA is an organic base such as a purine or pyrimidine or a derivative thereof. A nucleobase may be a canonical base (e.g., adenine, guanine, uracil, and cytosine) or a non-canonical or modified base including one or more substitutions or modifications including but not limited to alkyl, aryl, halo, oxo, hydroxyl, alkyloxy, and/or thio substitutions; one or more fused or open rings; oxidation; and/or reduction.

The mRNA may include a 5' untranslated region, a 3' untranslated region, and/or a coding or translating sequence. Optionally, the mRNA includes one or more of a stem loop, a chain terminating nucleoside, a polyA sequence, a polyadenylation signal, and/or a 5' cap structure.

A mRNA may include any number of base pairs, including tens, hundreds, or thousands of base pairs. Any number (e.g., all, some, or none) of nucleobases, nucleosides, or nucleotides may be an analog of a canonical species, substituted, modified, or otherwise non-naturally occurring. In a particular embodiment, the mRNA is modified. Substitutions and modifications to the mRNA of the present invention may be performed by methods readily known to one or ordinary skill in the art.

As used herein, "modified" means non-natural. That is, a mRNA may include one or more nucleobases, nucleosides, nucleotides, or linkers that are non-naturally occurring. In said embodiment, the mRNA can comprise at least one modification which confers increased or enhanced stability to the nucleic acid, including, for example, improved resistance to nuclease digestion in vivo. As used herein, the terms "modification" and "modified" as such terms relate to the nucleic acids provided herein, include at least one alteration which preferably enhances stability and renders the mRNA more stable (e.g., resistant to nuclease digestion) than the wild-type or naturally occurring version of the mRNA. As used herein, the terms "stable" and "stability" as such terms relate to the nucleic acids of the present invention, and particularly with respect to the mRNA, refer to increased or enhanced resistance to degradation by, for example nucleases (i.e., endonucleases or exonucleases) which are normally capable of degrading such mRNA. Increased stability can include, for example, less sensitivity to hydrolysis or other destruction by endogenous enzymes (e.g., endonucleases or exonucleases) or conditions within the target cell or tissue, thereby increasing or enhancing the residence of such mRNA in the target cell, tissue, subject and/or cytoplasm. Also contemplated by the terms "modification" and "modified" as such terms related to the mRNA of the present invention are alterations which improve or enhance translation of mRNA nucleic acids, including for example, the inclusion of sequences which function in the initiation of protein translation (e.g., the Kozac consensus sequence).

In a further embodiment, the mRNA of the invention has undergone a chemical or biological modification to render it more stable. Exemplary modifications to a mRNA include the depletion of a base (e.g., by deletion or by the substitution of one nucleotide for another) or modification of a base, for example, the chemical modification of a base. The phrase "chemical modifications" as used herein, includes modifications which introduce chemistries which differ from those seen in naturally occurring mRNA, for example, covalent modifications such as the introduction of modified nucleotides, (e.g., nucleotide analogs, or the inclusion of pendant groups which are not naturally found in such mRNA molecules).

In addition, suitable modifications include alterations in one or more nucleotides of a codon such that the codon encodes the same amino acid but is more stable than the codon found in the wild-type version of the mRNA. For example, an inverse relationship between the stability of RNA and a higher number cytidines (C's) and/or uridines (U's) residues has been demonstrated, and RNA devoid of C and U residues have been found to be stable to most RNases [30]. In some embodiments, the number of C and/or U residues in an mRNA sequence is reduced. In a another embodiment, the number of C and/or U residues is reduced by substitution of one codon encoding a particular amino acid for another codon encoding the same or a related amino acid. The term modification also includes, for example, the incorporation of non-nucleotide linkages or modified nucleotides into the mRNA sequences of the present invention (e.g., modifications to one or both the 3' and 5' ends of an mRNA molecule encoding a functional secreted protein or enzyme). Such modifications include the addition of bases to an mRNA sequence (e.g., the inclusion of a poly A tail or a longer poly A tail), the alteration of the 3' UTR or the 5' UTR, complexing the mRNA with an agent (e.g., a protein or a complementary nucleic acid molecule), and inclusion of elements which change the structure of an mRNA molecule (e.g., which form secondary structures).

In a particular embodiment, the nanoparticle of the present invention comprises a modified mRNA, more specific a nucleoside-modified mRNA, wherein naturally occurring modified nucleotides are incorporated into the mRNA transcript, with partial (at least 10%) and up to complete substitution (e.g. 10-100%, 20-100%, 30-100%, 40-100%, 50-100% etc.). Preferred nucleotides are pseudouridine (Ψ), N1-methylpseudouridine (m1Ψ) and/or 5-methylcytidine (5meC). By using nucleoside-modified mRNA, the intracellular mRNA recognition by TLR3, TLR7, and TLR8 can be reduced, which makes the mRNA 'immunosilent' and avoids the release of type I IFNs. Furthermore, nucleotide modifications can render the RNA more resistant to enzymatic degradation. However this comes together with a loss of RNA's self-adjuvant-effect, affecting hence DC activation and T-cell priming. In the present invention we demonstrated that the incorporation of a low amount of an iNKT agonist, more in particular α-GalCer or analog, ensures both a high antigen expression as well as a strong immune activation but without the strong induction of type I IFNs.

In one embodiment, the invention relates to a cationic and/or lipid-based nanoparticle in which both nucleoside-modified mRNA and an adjuvant such as an iNKT agonist provided herein can be complexed. As used herein, the term "complexed" includes the conjugation, encapsulation, attachment or coupling of the adjuvant with or in the nanoparticle. The term "admixed" refers to the adjuvant that is dissolved, dispersed, or suspended in the nanoparticle. The iNKT agonist is associated with, covalently coupled to, or incorporated/encapsulated in the nanoparticle by methods well known to the person skilled in the art or by the method as provided herein. As an example, the iNKT agonist can be incorporated in the aqueous core and/or the lipid membrane of lipid-based nanoparticles as provided herein, the iNKT agonist can be part of a lipidic or polymeric micelle formulation, or the iNKT agonist can be applied in polymeric nanoparticles such as polymer conjugates, polymer matrix nanoparticles and solid polymer nanoparticles.

The amount of mRNA in a nanoparticle composition may depend on the size, sequence, and other characteristics of the mRNA. The amount of mRNA in a nanoparticle composition may also depend on the size, composition, desired target, and other characteristics of the nanoparticle composition. The relative amounts of mRNA and other elements (e.g., lipids) may also vary. In one embodiment, the wt/wt ratio of the lipid component to an mRNA in a nanoparticle composition may be from about 1:1 to about 100:1. For example, the wt/wt ratio of the lipid component to a mRNA may be from about 5:1 to about 50:1. The amount of mRNA in a nanoparticle composition may, for example, be measured using fluorescence spectroscopy (e.g., Fluorescence correlation spectroscopy). In some embodiments, the one or more mRNAs, lipids, and amounts thereof may be selected to provide a specific N:P ratio. The N:P ratio of the composition refers to the molar ratio of nitrogen atoms in one or more lipids to the number of phosphate groups in an mRNA. The one or more mRNA, lipids, and amounts thereof may be selected to provide an N:P ratio from about 1:2 to about 6:1, such as 1:2, 1:1, 2:1, 3:1, 4:1, 5:1, and 6:1, and in particular from about 1:1 to 3:1.

In a further embodiment, the mRNA encodes any polypeptide or antigen of interest, including any naturally or non-naturally occurring or otherwise modified polypeptide or peptide epitope(s).

A polypeptide encoded by an mRNA may be of any size and may have any secondary structure or activity. In some embodiments, a polypeptide encoded by an mRNA may have an (indirect) therapeutic effect when expressed in a cell. In a further embodiment, the method of the invention comprises loading or transfecting the nanoparticle with an antigen encoding-nucleic acid, in particular RNA, more in particular mRNA. As used herein, the "antigen" is not limiting to the invention. In one embodiment, the antigen is selected from the group consisting of a tumor-antigen, a tumor-associated antigen, a cancer-testis antigen, a mutanome-derived antigen, a (oncogenic) viral antigen, a bacterial antigen, a yeast antigen, a parasitic antigen and a fungal antigen. The nanoparticle formulation of the present invention demonstrate that high transfection efficacies improve the likelihood that appropriate dosages of the mRNA will be delivered to the target cell, while minimizing potential (systemic) adverse effects.

Preparation of nanoparticles comprising mRNA can be by any method known to the skilled person, such as via ethanol dilution, lipid film hydration, or by the use of microfluidic devices. An exemplary method of preparing the mRNA loaded lipid-based nanoparticles of the present invention include the following steps: (1) dissolve appropriate amounts of lipids in chloroform, (2) add an appropriate amount of the iNKT agonist, (3) evaporate the chloroform and rehydrate the resulting lipids in a buffer, (4) reduce the size of the resulting lipid particles through sonication or extrusion, (5) mix with mRNA.

As used herein, an "iNKT cell agonist" has its general meaning in the art and refers to any derivative or analog derived from a lipid, that is typically presented in a CD1d context by antigen presenting cells (APCs) and that can activate iNKT cells, i.e. promote, in a specific manner, cytokine production by iNKT cells. In one specific embodiment, the iNKT cell agonist according to the invention is a glycolipid antigen such as α-Galactosylceramide (α-Gal-Cer; (2S,3S,4R)-1-O-(alpha-D-galactosyl)-N-hexaco-sanoyl-2-amino-1,3,4-octadecanetriol) having the common name KRN7000, and is an agelasphin derivative. As used herein, the term "α-galactosylceramide compound" or "α-GalCer compound" has its general meaning in the art and includes a functional derivative or analog derived from a glycosphingolipid that contains a galactose carbohydrate attached by an a-linkage to a ceramide lipid that has an acyl and sphingosine chains of variable lengths. A functional analog or derivative retains the capacity to activate iNKT cells. Various publications have described α-GalCer compounds and their synthesis. Functional derivatives or analogs of α-galactosylceramide, are provided in e.g. WO2014001204 (incorporated by reference and specifically referring to the disclosed compounds NU-αGC, PyrC-αGC and OCH), WO201379687, and WO2013162016. Examples of iNKT cell agonists include: HS44, BbGL-II, threitolcer-amide, ABX196, PBS-25, PBS-57, α-C-GalCer, OCH, Naphtylureum-α-GalCer or NU-α-GalCer, Alpha-GalCer-6"-(4-pyridyl)carbamate or PyrC-α-GalCer, (3S,4S,5R)-1-(6"-O-(4-pyridinylcarbamoyl)-α-C-D-galacto-pyranosyl)-3-hexacosylamino-nonadecane-4,5-diol, (3S,4S,5R)-1-(6"-O-(4-pyridinylcarbamoyl)-α-C-D-galacto-pyranosyl)-3-hexacosylamino-1-nonadecene-4,5-diol, (3S,4S,5R)-1-(6"-naphtureido-6"-deoxy-α-C-D-galacto-pyranosyl)-3-hexacosylamino-nonadecane-4,5-diol, (3S,4S,5R)-1-(6"-naphtureido-6"-deoxy-α-C-D-galacto-pyranosyl)-3-hexacosylamino-1-nonadecene-4,5-diol, α-1C-GalCer, or 7DW8-5. α-GalCer compounds can be chemically synthe-sized by methods known to the skilled person. In a particular embodiment of the present invention, the α-GalCer com-pound is incorporated in the lipid component of the nan-oparticle provided herein.

Strikingly, the iNKT cell agonist in the use and methods of the present invention, in particular a nanoparticle, is at about 3- to 5-fold more potent than the same agonist in solution. In comparison to prior art mRNA vaccines, in particular lipid nanoparticles composed with unmodified mRNA, 4-to-5 times higher numbers of antigen-specific T cells can be obtained in the present invention. The concen-tration of the iNKT cell agonist, in particular the α-GalCer compound, more in particular α-GalCer, in the nanoparticle is between 0.0015 mol % and 1 mol % of the total lipid amount, in particular, in between 0.0015 mol % and 0.5 mol %, more in particular between 0.0015 mol % and 0.25 mol %, even more in particular between 0.0015 mol % and 0.15 mol %.

The phrases "activate iNKT cells" or "induce iNKT immune response" have similar meanings and refer for instance to the observed induction of cytokine production, such as IFN-γ in iNKT cells by α-GalCer compound. Analysis of cytokine (e.g. IFN-γ) production by iNKT cells can be performed by the methods provided herein or by flow cytometry using CD1d tetramers loaded with αGalCer or derivates such as PBS-57.

Composition/Formulation

The invention further provides a pharmaceutical compo-sition, formulation or delivery system comprising the nanoparticle as provided herein, i.e. containing the genetic material such as the mRNA and the iNKT cell agonist, and one or more of a pharmaceutically acceptable excipient, carrier and/or diluent.

For example, the (pharmaceutical) composition may include one or more pharmaceutically acceptable excipients or accessory ingredients such as, but not limited to, one or more solvents, dispersion media, diluents, dispersion aids, suspension aids, granulating aids, disintegrants, fillers, gli-dants, liquid vehicles, binders, surface active agents, iso-tonic agents, thickening or emulsifying agents, buffering agents, lubricating agents, oils, and preservatives. Excipi-ents such as waxes, butters, coloring agents, coating agents, flavorings, and perfuming agents may also be included. Pharmaceutically acceptable excipients are well known in the art (see for example Remington's The Science and Practice of Pharmacy, 21$^{st}$ Edition, A. R. Gennaro; Lippin-cott, Williams & Wilkins, Baltimore, Md., 2006).

The pharmaceutically acceptable excipient may be a solid (e.g. calcium phosphate, magnesium stearate, talc, sugars, lactose, dextrin, starch, gelatin, cellulose, polyvinylpyrroli-dine, low melting waxes and ion exchange resins), a gel or a liquid. Suitable examples of liquid excipients for oral and parenteral administration include water (partially containing additives as above, e.g. cellulose derivatives, preferably sodium carboxymethyl cellulose solution), alcohols (includ-ing monohydric alcohols and polyhydric alcohols, e.g. gly-cols) and their derivatives, and oils (e.g. fractionated coco-nut oil and arachis oil). For parenteral administration, the excipient can also be an oily ester such as ethyl oleate and isopropyl myristate. Sterile liquid excipients are useful in sterile liquid form compositions for parenteral administra-tion. Liquid pharmaceutical compositions, which are sterile solutions or suspensions, can be utilised by, for example, subcutaneous, intranodular, intrathecal, epidural, intraperi-toneal, intravenous and intramuscular injection. In one embodiment, the composition is lyophilized.

In order to support the medical effect, i.e., in particular, the immune response, the pharmaceutical composition may, in an embodiment of the invention, also comprise further active compounds, where simultaneous or successive administration is conceivable. The therapeutic effect of the pharmaceutical composition according to the invention can arise, for example, through certain antitumor medicaments having a better action through activation of the complement system as a desired side effect or through the number of side effects of these medicaments being reduced by the reduction in the dose. As such, the uses and methods disclosed herein can also include the use of a nanoparticle or composition as described herein together with one or more additional (thera-peutic) agents for the treatment of disease conditions. In one example, said therapeutic agents are selected from chemo-therapeutic agents, biotherapeutic agents, immunogenic agents, immune stimulating cytokines and cells transfected with genes encoding immune stimulating cytokines. The combination of active ingredients may be: (1) incorporated in the present nanoparticle as such, e.g. as a further mRNA; (2) co-formulated and administered or delivered simultane-ously in a combined formulation; (3) delivered (e.g. by alternation, subsequently or in parallel) as separate formu-lations; or (3) by any other combination therapy regimen known in the art. When delivered in alternation therapy, the methods described herein may comprise administering or delivering the active ingredients sequentially, e.g., in sepa-rate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used. In some cases, a compound disclosed herein is administered and/or formulated with a second therapeutic.

In a specific embodiment, the second therapeutic or agent can be one or more of a chemotherapeutic or an immunotherapeutic agent. A specific immunotherapeutic agent for use in the combination therapies disclosed herein includes a so called "checkpoint inhibitor". During the last few years, in addition to therapy concepts based on oncolytic viruses, the field of immuno-oncology has become a valuable approach in the fight against cancer. One of the most recent promising approaches to activate therapeutic antitumor immunity is the blockade of immune checkpoints. Immune checkpoints refer to a plethora of inhibitory pathways hardwired into the immune system that are crucial for maintaining self-tolerance and modulating the duration and amplitude of physiological immune responses in peripheral tissues in order to minimize collateral tissue damage. It is now clear that tumors co-opt certain immune-checkpoint pathways as a major mechanism of immune resistance, particularly against T cells that are specific for tumor antigens. Because many of the immune checkpoints are initiated by ligand-receptor interactions, they can be readily blocked by antibodies or modulated by recombinant forms of ligands or receptors. An important immune checkpoint receptor is cytotoxic T-lymphocyte-associated antigen 4 (CTLA4; also known as CD152), which down modulates the amplitude of T cell activation. The approved anti-CTLA4 antibody is known under the name "ipilimumab" and marketed under the brandname "Yervoy®" by Bristol Myers Squibb (BMS). Another important immune-checkpoint receptor is programmed cell death protein 1 (PD1), and limits T cell effector functions within tissues. The humanized monoclonal antibody pembrolizumab (also known as MK-3575 or Keytruda® marketed by Merck Sharp Dohme; MSD) is directed against the target PD-1. Another anti-PD1 antibody is nivolumab; Opdivo® marketed by Bristol Myers Squibb; BMS). Hence, in a particular embodiment, the checkpoint inhibitor is a CTLA-4 inhibitor or antagonist, specifically binding CTLA-4. In a further embodiment, the checkpoint inhibitor is a PD-1 and CTLA-4 bispecific molecule. Such bispecific molecules are capable of specifically binding to PD-1 and CTLA-4 molecules that are present on the surfaces of exhausted and tolerant tumor-infiltrating lymphocytes and other cell types.

In a particular embodiment, the checkpoint inhibitor is a programmed cell death protein 1 (PD-1) inhibitor, or a programmed death ligand (PD-L1) or (PD-L2) inhibitor. The term "inhibitor" or "antagonist" refers to any chemical compound or biological molecule that impairs the ability of such cell-surface molecules to respond to their respective ligand, e.g. a compound or molecule that blocks binding of PD-L1 expressed on a cancer cell to PD-1 expressed on an immune cell (T-cell, B-cell, or NKT-cell) and/or blocks binding of PD-L2 expressed on a cancer cell to the immune-cell expressed PD-1. Alternative names or synonyms for PD-1 and its ligands include: PDCD1, PD1, CD279, and SLEB2 for PD-1; PDCD1L1, PDL1, B7H1, B7-4, CD274, and B7-H for PD-L1; and PDCD1L2, PDL2, B7-DC, Btdc, and CD273 for PD-L2. In one embodiment, the PD-1 inhibitor blocks binding of human PD-L1 to human PD-1, and preferably blocks binding of both human PD-L1 and PD-L2 to human PD-1. Human PD-1 amino acid sequences can be found in NCBI Locus No.: NP005009. Human PD-L1 and PD-L2 amino acid sequences can be found in NCBI Locus No.: NP054862 and NP079515, respectively.

In one embodiment, said inhibitor includes antibodies and antigen-binding fragments thereof. In the alternative, PD-1 or PD-L1(2) binding moieties or antagonists can be used which include a variety of different types of molecules including those that specifically bind resp. PD-1 or PD-L1 (2). Such ligands include small molecules, polypeptides (e.g. a fusion protein) or nucleic acids (aptamers, siRNA, shRNA, etc), and the like.

The term "antibody" refers to polyclonal antibodies, monoclonal antibodies (mAbs), chimeric antibodies, humanized antibodies, a human engineered antibody, a human antibody, as well as antigen binding antibody fragments and molecules having antigen binding functionality. More in particular, the term "antibody" includes an intact immunoglobulin having four polypeptide chains, two heavy (H) chains and two light (L) chains linked by disulfide bonds. The term "antibody" also includes PD-1 or PD-L1(2) binding antibody fragments such as a Fab fragment, a Fab' fragment, a F(ab')2 fragment, a Fd fragment, a Fv fragment, a scFv fragment, a domain antibody (dAb), heavy chain antibodies (hcAb), minibodies, a variable domain of camelid heavy chain antibody (VHH or Nanobody®), a variable domain of the new antigen receptor (VNAR) and engineered CH2 domains (nanoantibodies). Also peptides and scaffolds with antibody like characteristics can be used, such as single chain antiparallel coiled protein (alphabodies). Active fragments can be derived from an antibody by a number of art-known techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. Anti-PD-L1 and anti-PD-1 antibodies and methods of making the same are known in the art.

An anti-PD-1 antibody or anti-PD-L1 antibody is capable of specifically binding PD-1 or PD-L1(2). Such antibodies are commercially available or can be generated by methods generally known to the skilled person. An exemplary anti-PD-L1 antibody is Atezolizumab (Tecentriq® marketed by Roche) or Avelumab (Bavencio®, marketed by Merck). Anti-PD-L1 antibody blocks its binding to and activation of its receptor PD-L1, which may enhance the T-cell-mediated immune response to neoplasms and reverse T-cell inactivation in chronic infections disease. PD-L1 is expressed broadly on hematopoietic and parenchymal tissues.

It is crucial that the pharmaceutical composition comprises, as active compound, an effective amount of the nanoparticles and/or dispersion thereof together with the pharmaceutically tolerated assistants. The terms "effective amount" or "effective dose" are used interchangeably herein and denote an amount of the pharmaceutical active compound which has a prophylactically or therapeutically relevant action on a disease or pathological change. A "prophylactic action" prevents the outbreak of a disease or even infection with a pathogen after ingress of individual representatives in such a way that subsequent spread thereof is greatly reduced or they are even completely deactivated. A "therapeutically relevant action" frees from one or more disease symptoms or results in the partial or complete reversal of one or more physiological or biochemical parameters which are associated with or causally involved in the disease or pathological change, into the normal state. The respective dose or dose range for the administration of the nanoparticles according to the invention is sufficiently large to achieve the desired prophylactic or therapeutic effect of induction of an immune response. In addition, the composition can be used as "adjuvant therapy" given in addition to a primary or initial therapy to maximize its effectiveness in a curative setting, or as a "maintenance" or "consolidative" therapy subsequent to and initial therapy to maximize disease control and delay disease recurrence.

In general, the dose will vary with the age, constitution and gender of the patient, and the severity of the disease will be taken into account. The specific dose, frequency and duration of administration are, in addition, dependent on a multiplicity of factors, such as, for example, the targeting and binding ability of the nanoparticles, nutrition habits of the individual to be treated, type of administration, excretion rate and combination with other medicaments. The individual dose can be adjusted both with respect to the primary disease and also with respect to the occurrence of any complications. The precise dose can be established by a person skilled in the art using known means and methods. This teaching of the invention is valid for and applicable without restrictions to the pharmaceutical composition comprising the nanoparticles and/or dispersions thereof, so long as it appears appropriate.

Application

The invention provides first and further medical uses of the nanoparticles, compositions or combinations as provided herein.

The nanoparticles, compositions and methods of the invention provide for the delivery of nucleic acids, in particular mRNA, to treat a number of disorders. In particular, the present nanoparticles and/or nanoparticle dispersions are suitable for the prophylactic or therapeutic treatment of diseases which are selected from the group of cancer, infectious diseases, tumors, autoimmune diseases, allergies and chronic or acute inflammation processes.

The term "infectious disease" as used herein refers to any kind of clinically evident disease resulting from the presence of pathogenic microbial agents, including pathogenic viruses, pathogenic bacteria, fungi, protozoa, or multicellular parasites.

The invention also relates to the nanoparticles and compositions according to the invention for use in immunoprophylaxis or immunotherapy. The invention furthermore relates to the use of an effective amount of the nanoparticles according to the invention for the preparation of a vaccine for immunoprophylaxis or immunotherapy.

In one aspect, the current invention is directed to the development of a (therapeutic) vaccine that evokes an adaptive immune response against cancer by the delivery of mRNA encoding tumor antigens as provided herein and using the nanoparticles as described herein.

The disclosed compositions and methods are particularly useful for treating cancer, for example, inhibiting cancer growth, including complete cancer remission, for inhibiting cancer metastasis, and for promoting cancer resistance. In the context of the present invention, the term "cancer" refers to any kind of disease provoked by a malignant tumor. The term "cancer growth" generally refers to any one of a number of indices that suggest change within the cancer to a more developed form. Thus, indices for measuring an inhibition of cancer growth include but are not limited to a decrease in cancer cell survival, a decrease in tumor volume or morphology (for example, as determined using computed tomographic (CT), sonography, or other imaging method), a delayed tumor growth, a destruction of tumor vasculature, improved performance in delayed hypersensitivity skin test, an increase in the activity of cytolytic T-lymphocytes, and a decrease in levels of tumor-specific antigens. The term "cancer resistance" refers to an improved capacity of a subject to resist cancer growth, in particular growth of a cancer already had. In other words, the term "cancer resistance" refers to a decreased propensity for cancer growth in a subject.

In one aspect, the cancer comprises a solid tumor, for example, a carcinoma and a sarcoma. Carcinomas include malignant neoplasms derived from epithelial cells which infiltrate, for example, invade, surrounding tissues and give rise to metastases. Adenocarcinomas are carcinomas derived from glandular tissue, or from tissues that form recognizable glandular structures. Another broad category of cancers includes sarcomas and fibrosarcomas, which are tumors whose cells are embedded in a fibrillar or homogeneous substance, such as embryonic connective tissue.

The invention further provides a method for decreasing or inhibiting tumor growth, cancer cell invasion or metastasis in a subject having a cancer by administering the nanoparticle or composition of the invention to a subject having a cancer, wherein the nanoparticle is administered in an amount sufficient to decrease tumor growth, cancer cell invasion or metastasis in the subject. In a particular embodiment, the cancer cell is selected from the group consisting of: a breast cancer cell, a colon cancer cell, a kidney cancer cell, a lung cancer cell, a skin cancer cell, an ovarian cancer cell, a pancreatic cancer cell, a prostate cancer cell, a rectal cancer cell, a stomach cancer cell, a thyroid cancer cell, and a uterine cancer cell.

In a further embodiment the method of the invention includes the treatment of a metastatic cancer in a lymph node in a subject, wherein the nanoparticle or composition is administered to a lymph node of a subject having a metastatic cancer.

In a further aspect, the nanoparticle or composition can be used in a method for delivering and/or expressing an antigen to antigen presenting cells, preferably antigen presenting cells in the spleen and lung, and/or in a method for inducing an immune response, preferably an immune response against cancer, in a subject, said method comprising administering to the subject the nanoparticle or composition according to the invention.

An "antigen-presenting cell" as used herein is taken to mean any cell which can be induced to present antigens to a T-cell, which also includes precursor cells which can be differentiated and activated to antigen-presenting cells. Antigen-presenting cells include dendritic cells, Langerhans cells, PBMCs, macrophages, B lymphocytes or other activated or modified cell types, such as, for example, epithelial cells, fibroblasts and endothelial cells which express MHC molecules on their cell surfaces, but include preferably dendritic cells, particularly dendritic cells of the lymph nodes. Precursors of antigen-presenting cells include CD34+ cells, monocytes, fibroblasts and endothelial cells.

As used herein, the term "subject" refers to any animal (e.g., a mammal), including, but not limited to, humans, non-human primates, rodents, and the like, to which the compositions and methods of the present invention are administered. Typically, the terms "subject" and "patient" are used interchangeably herein in reference to a human subject.

Administration

One route of administration is intravenous administration. Additionally, the nanoparticle or composition comprising the nanoparticle may be delivered to a patient using any standard route of administration, including oral, rectal, vaginal, transmucosal, pulmonary including intratracheal or inhaled, or intestinal administration; parenteral delivery, including intramuscular, subcutaneous, intramedullary injections, as well as intrathecal, direct intraventricular, intravenous, intraperitoneal, intranasal, or intraocular injections.

In a particular embodiment, the administration is by intravenous (bolus or infusion) or intraperitoneal injection, or by inhalation or intratracheal or intranasal administration.

Alternately, the compositions of the invention may be administered in a local rather than systemic manner, for example, via injection of the pharmaceutical composition directly into a targeted tissue or tumor, e.g. in a sustained release formulation. Local delivery can be affected in various ways, depending on the tissue to be targeted. For example, aerosols containing compositions of the present invention can be inhaled (for nasal, tracheal, or bronchial delivery); compositions of the present invention can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection. Formulations containing compositions of the present invention complexed with therapeutic molecules or ligands can even be surgically administered, for example in association with a polymer or other structure or substance that can allow the compositions to diffuse from the site of implantation to surrounding cells. Alternatively, they can be applied surgically without the use of polymers or supports.

Administration may take the form of single dose administration, or the composition as disclosed herein can be administered over a period of time, either in divided doses or in a continuous-release formulation or administration method (e.g., a pump). The amounts of composition administered and the route of administration chosen should be selected to permit efficacious treatment of the disease condition. In one embodiment, the nanoparticle or composition of the present invention are administered to a subject one a day, twice a day, daily or every other day. In a preferred embodiment, the compositions of the present invention are administered to a subject twice a week, once a week, every ten days, every two weeks, every three weeks, or more particular every four weeks, once a month, every six weeks, every eight weeks, every other month, every three months, every four months, every six months, every eight months, every nine months or annually.

The combination or compositions of the invention may be used in a monotherapy for treating, ameliorating, reducing the risk of or preventing a disease. Alternatively, the combination or compositions may be used as an adjunct to, or in combination with, known therapies which may be used for treating, ameliorating, reducing the risk of or preventing a disease.

All of the features described herein (including any accompanying claims, abstract and drawings), and/or all of the steps of any method or process so disclosed, may be combined with any of the above aspects in any combination, except combinations where at least some of such features and/or steps are mutually exclusive. The invention will be further described by the following figures, tables and examples, which are not intended to limit the scope of protection as defined in the claims.

EXAMPLES

Materials and Methods

Cell Culture and Mice

Female C57BL/6 mice (6 weeks old) were purchased from Envigo (Gannat, France) and housed in an SPF facility. All animal experiments were conducted according to the regulations of the Belgian law and approved by the local Ethical Committee. Primary murine bone marrow-derived DC (BM-DC) cultures were generated as described by Verbeke et al. (2017).

The mouse melanoma cell line B16-OVA (kindly provided by K. Rock, University of Massachusetts Medical Center) and the T cell lymphoma E.G7-OVA (obtained from the American Type Culture Collection, Rockville, Md., USA) were cultured at 37° C. in a humidified 5% CO2 atmosphere in RPMI 1640 medium (Sigma-Aldrich, Diegem, Belgium) supplemented with 10% FBS, 100 U ml-1 penicillin, 100 μg ml-1 streptomycin, 2 mm l-glutamine and 0.4 mg ml of the selection agent G418 (Thermo-Scientific, Aalst, Belgium).

mRNA Constructs

Unmodified and nucleoside-modified (5meC, $\Psi$) mRNA encoding firefly luciferase (fLuc), and mRNA encoding for eGFP were purchased from TriLink (San Diego, CA). For the immunization studies, a truncated form of ovalbumin (tOVA) fused to the first 80 amino acids of the invariant chain (Ii80) was produced by in vitro mRNA transcription from pGEM-Ii80tOVA plasmids [24]. The plasmids were purified using a QIAquick PCR purification kit (Qiagen, Venlo, The Netherlands) and linearized using the Spe I restriction enzyme (Promega, Leiden, The Netherlands). Linearized plasmids were used as templates for the in vitro transcription reaction using the T7 MegaScript kit, including an Anti-Reverse Cap Analog (ARCA) and Poly (A) tailing reagents (Ambion, Life Technologies, Ghent, Belgium). For the transcription of modified mRNA, cytidine and uridine nucleotides were 100% replaced by 5-methylcytidine and pseudouridine (TriLink). The resulting mRNAs were purified by DNase I digestion, precipitated with LiCl and washed with 70% ethanol. The mRNA concentration was determined by measuring the absorbance at 260 nm. mRNAs were stored in small aliquots at –80° C. at a concentration of 1 μg μl$^{-1}$. mRNA encoding murine tyrosinase related protein 2 (TRP-2) was kindly provided by Prof. Karine Breckpot and Prof. Kris Thielemans. TRP-2 is known as a tumor-associated antigen expressed by B16 melanoma cells [34].

mRNA Lipid Nanoparticle Preparation

DOTAP (1,2-dioleoyl-3-trimethylammonium-propane) and cholesterol were purchased from Avanti Polar Lipids (Alabaster, USA). Alpha-Galactosylceramide (α-GalCer), Naphtylureum-α-GalCer (NU-α-GalCer), Alpha-GalCer-6"-(4-pyridyl)carbamate (Pyr-α-GalCer), (2S,3S,4R)-1-O-(α-D-Galactopyranosyl)-N-tetracosanoyl-2-amino-1,3,4-nonanetriol) (OCH) and FITC-labelled α-GalCer were provided by S. Van Calenbergh (Ghent University, Ghent, Belgium). Cationic liposomes of DOTAP-cholesterol (2:3 molar ratio) were prepared by transferring the appropriate amounts of lipids, dissolved in chloroform into a round-bottom flask. For liposomes formulated with α-GalCer, 0.5, 0.15, 0.015 or 0.0015 mol % of the total lipid amount was replaced by α-GalCer or the provided analog. The chloroform was evaporated under nitrogen, after which the lipid film was rehydrated in HEPES buffer (20 mM, pH 7.4, Sigma-Aldrich) to obtain a final lipid concentration of 12.5

μmol ml-1. The resulting cationic liposomes were sonicated until the dispersion became clear in a bath sonicator (Branson Ultrasonics, Dansbury, USA). Then, they were mixed with mRNA to obtain mRNA nanoparticles at a cationic lipid-to-mRNA (N/P) ratio of 3. mRNA nanoparticles for in vivo use were prepared in an isotonic HEPES buffer containing 5% glucose (Sigma-Aldrich).

The mRNA lipid nanoparticles composed with the "ionizable" amino lipid DLin-MC3-DMA were prepared in the lab of R. van der Meel as previously described [31]. Briefly, the appropriate lipids (Dlin-MC3-DMA, DSPC, cholesterol, PEG-DMG and α-GalCer) were dissolved in ethanol to a final concentration of 10 mM total lipid. The mRNA cargo was dissolved in 25 mM sodium acetate pH 4 buffer. Next, the two solutions were mixed at a cationic (amino) lipid-to-mRNA (N/P) ratio of 3 utilizing a T-junction mixer [32] (flow rate ratio 3:1 of aqueous (mRNA) and organic solution (lipids)). The resultant mixture was dialyzed against PBS (pH7.4) overnight and finally passed through a 0.22 μm filter. The total mRNA amount in the mRNA LNPs was measured using a Quant-iT™ RiboGreen™ RNA Assay Kit (Thermo-Scientific), in order to calculate the mRNA LNP dose for the mice studies. In one LNP formulation both fLuc mRNA and tOVAI80 mRNA (50:50) were combined.

Physicochemical Characterization of the mRNA Lipoplexes mRNA nanoparticles prepared at different N/P ratios in HEPES buffer were subjected to a size and zeta potential quality control using a Malvern Zetasizer nano-ZS (Malvern Instruments Ltd, Worcestershire, UK). To examine the complexation of mRNA to the liposomes and the stability of this interaction in serum-containing medium, mRNA nanoparticles were diluted and incubated in 50% FCI serum or 50% human serum. After 2h incubation at 37° C., Ambion loading buffer (Ambion) was added and mixtures were loaded into a 1% agarose gel in TBE buffer, to which GelRed (Biotium, Hayward, CA) was added for visualization of the mRNA. The gel was run for 30 min at 100 V and imaged under UV light. Samples containing only (unpackaged, i.e. so named 'naked') mRNA, only serum or serum together with naked mRNA, were run as controls. A molecular weight marker with bands at a range of 0.25 to 10 kb was included to provide size determination of the RNA (Promega, Leiden, The Netherlands).

To predict the colloidal stability of mRNA nanoparticles in serum, nanoparticles containing Cy5 labelled mRNA were incubated up to 24° h in 90% human serum at 37° C. Subsequently their size distribution was evaluated by fluorescence single particle tracking (fSPT) microscopy. fSPT allows to monitor the diffusion of fluorescently labelled nanoparticles in biological fluids [25]. By recording high-speed confocal movies of individually moving particles, motion trajectories of single particles can be visualized and their size distribution can be calculated. fSPT measurements on mRNA nanoparticles were performed as follows; first, 20 μl of Cy5 labelled mRNA nanoparticles was diluted in human serum (1:25) and incubated for 2 h, 6 h or 24 h at 37° C., after which 5 μl was added to 45 μl of human serum. The samples were then transferred to a black coated 96 well plate and placed on a swept-field confocal microscope (LiveScan Swept Field Confocal Microscope System; Nikon, Brussels, Belgium) equipped with a Plan Apo 60×1.0 NA oil immersion objective lens (Nikon) and a fast and sensitive EMCCD camera (Ixon Ultra 897; Andor Technology, CT, USA). The microscope was focused 20 μm above the bottom of the well plate and the Cy5-labelled mRNA nanoparticles were excited with a solid-state 125 mW 640 nm (Agilent Technologies, CA, USA) laser. For each sample, 20 movies of about 100 frames each were recorded at different random locations within the sample.

In Vitro Evaluation of mRNA Transfection, α-GalCer Delivery and α-GalCer Presentation by BM-DCs The in vitro experiments were performed on BM-DCs at day 6 of cell culture. The day before transfection, cells were seeded in 24 well plates at $5 \times 10^5$ cells per well, and grown in the cell culture medium with 5% FCI serum. The transfection efficiency of the mRNA lipoplexes was evaluated by using a eGFP reporter mRNA. To perform the transfection in OptiMem®, the cell culture medium was removed, eGFP mRNA lipoplexes dispersed in OptiMem® were added to the cells (1 μg mRNA per $5 \times 10^5$ cells) and after 2 h of incubation, cells were re-cultured in the cell culture medium with 5% FCI serum. For the delivery of α-GalCer, mRNA nanoparticles containing 0.5 mol % of α-GalCer were added directly to the cells in the complete cell culture medium (1 μg mRNA per $5 \times 10^5$ cells). The cellular uptake of α-GalCer was evaluated using α-GalCer labelled with a covalently coupled FITC-dye (provided by S. Van Calenbergh). To evaluate the presentation of α-GalCer in cell-surface CD1d complexes, BM-DCs cells were surface-stained with a monoclonal antibody specific for α-GalCer-CD1d complexes (clone L363, eBioscience). Flow analysis was performed 24h after the addition of mRNA nanoparticles (fLuc mRNA). Cells were collected and washed with PBS, stained with a fixable viability dye eFluor® 450 (eBioscience) according to the manufacturer's instructions, incubated with Fc block (CD16/32) to block non-specific FcR binding (BD Biosciences, Erembodegem, Belgium), and surface stained for CD11c-APC (clone N418) and α-GalCer:CD1d complex-PE for 30 min at 4° C. Mouse IgG2a kappa PE antibody was used as isotype control for the presentation of α-GalCer:CD1d. After additional washing steps, the cells were analysed by flow cytometry using a CytoFLEX (Beckman Coulter, Krefeld, Germany) and analysis was performed using FlowJo software (FlowJo, OR, USA). Confocal microscopy images of the cells were recorded using a Nikon C1si confocal laser scanning module attached to a motorized Nikon TE2000-E inverted microscope (Nikon Benelux, Brussels, Belgium), equipped with a Plan Apo 60×1.0 NA oil immersion objective lens (Nikon).

Administration of mRNA Nanoparticles and Anti-PD-L1 Antibodies

Mice were anesthetized in a ventilated anesthesia chamber with 3% isoflurane in oxygen. Prior to injection, a catheter of polyethylene tubing (Intramedic PE10, BD) containing sterile 0.9% NaCl solution was inserted in the tail vein. After correct placement, nanoparticles with the indicated cargo diluted in sterile 5% glucose HEPES buffer were slowly injected (200 μl containing 10 μg mRNA per mouse). The optimized dose of nanoparticle-encapsulated α-GalCer was 20 ng per mouse (0.015 mol %), determined based on cytokine production and iNKT activation. Anti-PD-L1 antibodies (10F.9G2, Bio X cell, West Lebanon, USA) or rat IgG2b isotype control antibodies (LTF-2, Bio X cell) were administered intraperitoneally at a dose of 100 μg, which were injected directly after the administration of mRNA nanoparticles.

Bioluminescence Imaging

Six hours after the administration (i.v., i.p., i.n. or i.t.) of nanoparticles containing fLuc mRNA, mice were anesthetized and abdomen and chest were depilated with hair removal cream. Subsequently, VivoGlo™ Luciferin (Promega) was administered intraperitoneally in a volume of 100

μl (33 mg ml-1) per mouse. After 5-10 min bioluminescence images were acquired by the IVIS lumina II system (PerkinElmer, Waltham, Mass.).

Therapeutic Vaccination Experiments

The therapeutic potential of mRNA nanoparticles (containing different cargo, or in combination with anti-PD-L1 antibodies) was evaluated by performing therapeutic vaccinations in tumor-bearing mice. For this, C57BL/6 received a s.c. injection of ×10$^5$ E.G7-OVA, B16-OVA or B16F0 tumor cells (suspended in PBS) in the flank. 8 days after tumor inoculation, when the lesions were palpable, the mice were randomized in different treatment groups based on tumor volume, and vaccinated via the intravenous route with mRNA nanoparticles. In some experiments, animals received a second and third therapeutic vaccination. Tumor growth was measured every other day or 2 days using a digital caliper. When the tumor volume exceeded 1000 mm$^3$ (B16-OVA, B16F0) or 1500 mm$^3$ (E.G7-OVA), the mice were euthanized via cervical dislocation.

Flow Cytometric Analysis on Single Cell Suspensions

At different time points after immunization, mice were sacrificed and spleen, lungs, liver or tumors were harvested and processed into single cell suspensions as described in [18]. Single cell suspensions were stained with either a fixable viability dye eFluor® 450 (Thermo Scientific) or Zombie Yellow™ (Biolegend, San Diego, CA) according to the manufacturer's instructions to exclude dead cells from analysis, incubated with Fc block (CD16/32) to block non-specific FcR binding (BD Biosciences, Erembodegem, Belgium), and surface stained with the indicated antibodies during 30 min at 4° C. (all Thermo-Scientific). After additional washing steps, the cells were analyzed by flow cytometry. Compensation for spectral overlap was calculated using UltraComp eBeads™ Compensation Beads (Thermo-Scientific) stained with individual fluorochrome-conjugated antibodies.

The activation state of DC positive for CD11c-(APC or FITC) in the spleen was analysed by measuring the up-regulation of the co-stimulatory molecules CD40-FITC (HM40-3), CD86-FITC (CL1), CD80-PE/Cy7 (16-10A1), and the inhibitory molecule PD-L1-Super Bright 436 (MIH5). T cells were stained with monoclonal antibodies, including CD3e-PE (145-2C11), CD4-FITC (GK1.5), CD8a-(APC or AF488) (53-6.7) and PD-1-(efl450 or FITC) (RMP1-30). To stain OVA selective T cells, BV450-conjugated H-2Kb/SIINFEKL tetramer (OVA-tetramer) were used, obtained from the National Institutes of Health (NIH) Tetramer Core Facility. iNKT cells were stained with TCRβ-APC (H57-597), PD1-efl450 and mCD1d PBS-57 PE tetramer obtained from the NIH tetramer Core Facility. NK cells were detected using CD3e-PE (negative gating) and NK1.1-APC (PK136) staining. In addition, myeloid derived suppressor cells (MDSCs) and tumor associated macrophages (TAMs) were stained with antibodies including, CD11b-PE/Dazzle™ 594 (Biolegend), MHC-II-efl450 (M5/ 114.15.2), F4/80-(FITC or AF700) (6F12), Ly-6G/Ly-6C-FITC (RB6-8C5) and CD206-APC (C068C2). DCs (CD11c$^+$) and tumor cells (CD45-PerCP-Cy5.5 negative cells) were evaluated for the expression of PD-L1.

Cytokine Measurements and Alanine Transaminase (ALT) Activity.

Serum was collected 6h after i.v. injection of the mRNA nanoparticles and samples were stored at −80° C. Mouse Platinum IFN alpha ELISA kit, IFN-γ and IL-4 ELISA kits (Ready-SET-Go!®) were purchased from Thermo-Scientific. A panel of 13 other cytokines, including IL-1α, IL-1β, IL-6, IL-10, IL-12p70, IL-17A, IL-23, IL-27, MCP-1, IFN- β, IFN-γ, TNF-α, and GM-CSF, was quantified using a multiplex assay (LEGENDplex™ Mouse Inflammation Panel, Biolegend). ALT enzyme activity was measured using a colometric assay kit (MaxDiscovery™, Bioo Scientific Corporation, Austin, USA). All assays were performed according to the manufacturer's instructions.

Statistical Analysis

All data are presented as mean±standard deviation. Presented data of the in vitro experiments are representative for at least 3 independent experiments performed on 3 different days. The in vivo experiments contain data of at least two experiments merged into a single graph, this is explicitly mentioned in the figure caption. Statistical analyses were performed using a One-Way ANOVA followed by Tukey's post hoc test (GraphPad Prism6, La Jolla, CA, USA). Asterisks indicate statistical significance (*, $p<0.05$; , $p<0.01$; *, $p<0.001$). Survival was visualized in a Kaplan-Meier plot. Differences in survival were analyzed by the log-rank (Mantel-Cox) test.

Results 1. mRNA Galsomes Have Superior Therapeutic Outcome Over mRNA Nanoparticles Combined With Classical Adjuvants.

In previous research [18], we showed that co-delivering a TLR agonist (MPLA) with nucleoside-modified mRNA lipoplexes is feasible and can be used to promote innate immune activation. However, for a therapeutic application in e.g. cancer, FIG. 1 shows that the immune responses obtained with mRNA nanoparticles with relative high doses of MPLA (2 μg per mouse) could not break the immune tolerance and inhibit the tumor growth in established E.G7-OVA tumors. In sharp contrast, we found that the administration of mRNA nanoparticles containing the iNKT agonist α-GalCer, referred to herein as 'mRNA Galsomes', was effective in achieving tumor regression. Interestingly, these results with α-GalCer were obtained with a 100 times lower dose of adjuvant (0.020 μg α-GalCer per mouse), than what was used for mRNA nanoparticles with MPLA (2 μg MPLA per mouse).

2. Physicochemical Characterization and Stability of mRNA Nanoparticles in Serum We initially evaluated mRNA nanoparticles with a different lipid composition. The mRNA nanoparticles were composed of the cationic lipid DOTAP (1,2-dioleoyloxy-3-trimethylammonium propane chloride) or DC-Cholesterol (3β-[N—(N',N'-dimethylaminoethane)-carbamoyl]cholesterol), and a helper lipid, either DOPE (1,2-dioleoyl-sn-glycero-3-phosphoethanolamine) or cholesterol. Lipofectamine RNAiMAX mRNA nanoparticles were prepared as described in (Broos et al. 2016).

Figure 2:
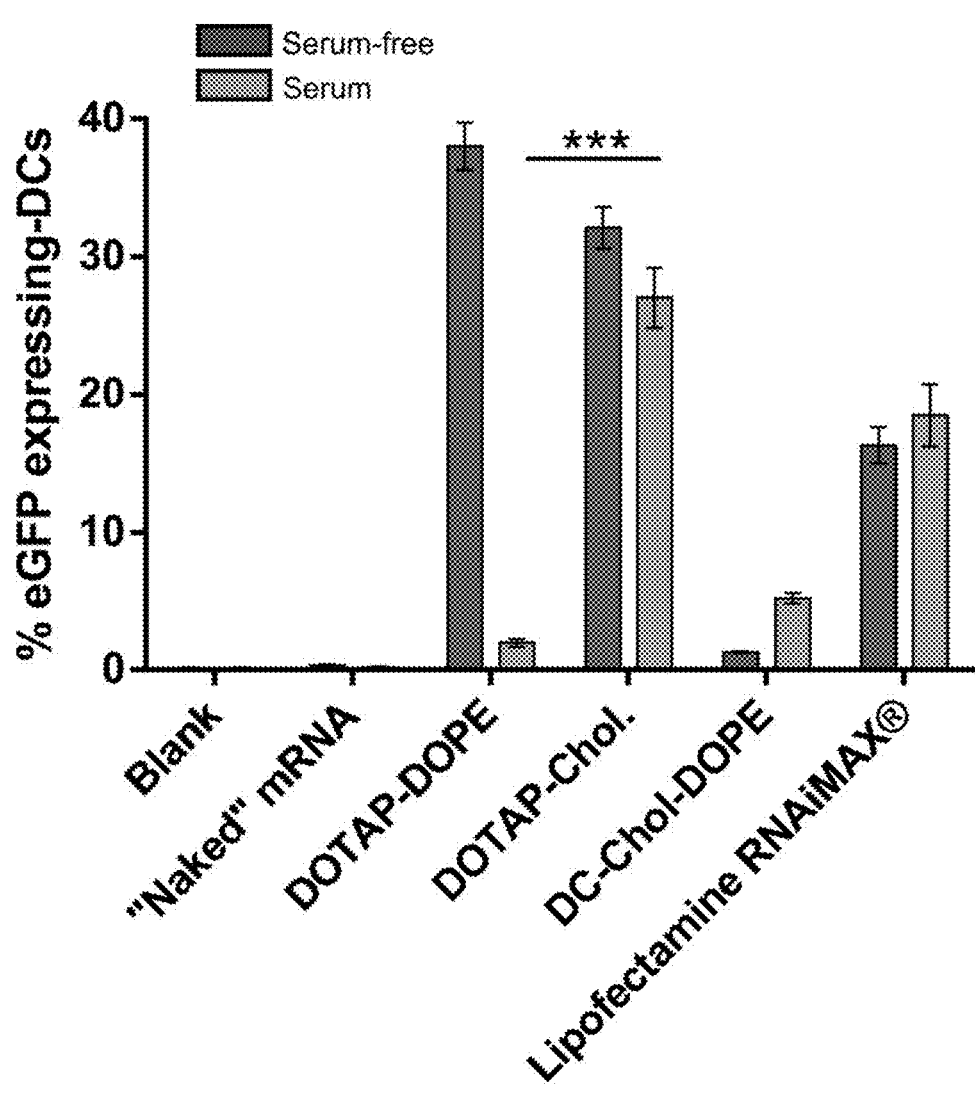
FIG. 2. Transfection efficiency of DOTAP-cholesterol versus other lipid formulations for mRNA delivery. (A) Percentage of enhanced green fluorescent protein (eGFP) transfected BM-DCs 24 h after the cells were incubated with mRNA packaged in DOTAP-cholesterol-, DOTAP-DOPE, DC-cholesterol-DOPE, or Lipofectamine® RNAiMAX nanoparticles (using unmodified mRNA). Transfections were performed in serum-free medium (OptiMem®) and serum-containing medium (5% Hyclone™ FetalClone ISerum). DCs were gated based on CD11c surface staining.

Interestingly, we found that DOTAP-cholesterol mRNA nanoparticles were superior in transfecting murine bone marrow-derived (BM)-DCs over the widely reported DOTAP-DOPE mRNA nanoparticles, or the commercial transfection Lipofectamine RNAiMAX. FIG. 2 shows that following exposure to serum, DOTAP-DOPE mRNA nanoparticles (nearly) failed in transfecting (BM)-DCs while DOTAP-cholesterol mRNA nanoparticles were successful, making them better suited for in vivo use.

Figure 3:
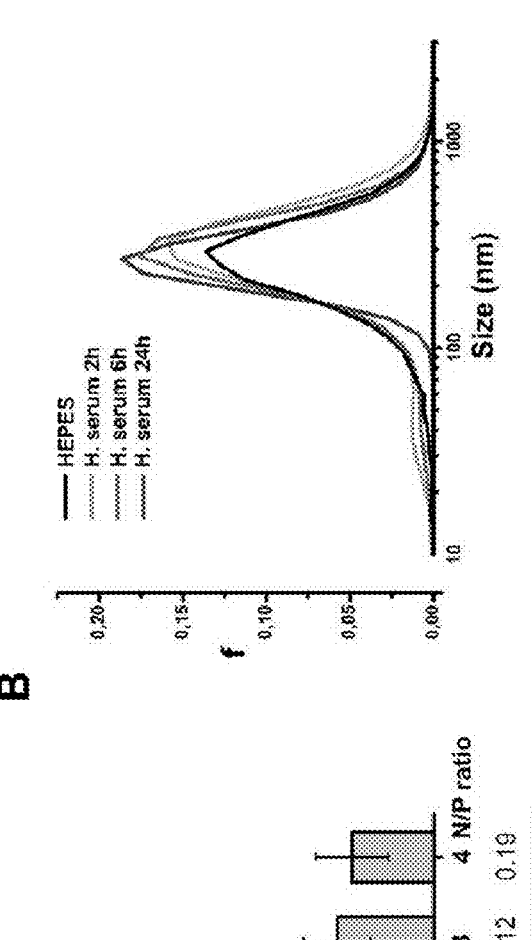
FIG. 3. Physicochemical characterization of mRNA nanoparticles. (A) Size (Z average), polydispersity index (PdI) and zeta potential of mRNA nanoparticles (dose of 1 µg mRNA) dispersed in HEPES buffer at increasing N/P ratios. (B) Size analysis (by fSPT) on mRNA nanoparticles (Cy5-labelled mRNA) at a N/P ratio of 2.5:1, dispersed in HEPES buffer, or incubated in human serum at 37° C. for 2 h, 6° h and 24 h.
Figure 3:
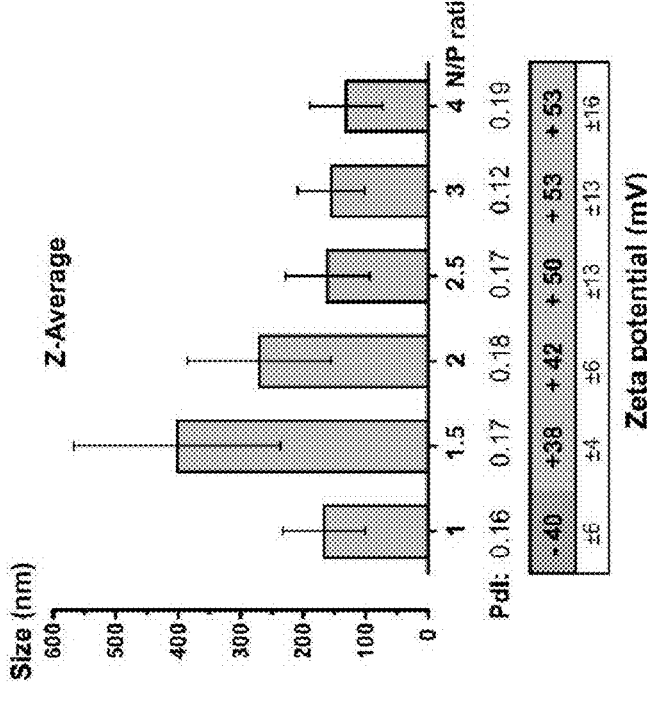

We focused on the behavior of DOTAP-cholesterol mRNA nanoparticles in serum (in vitro). To assure complete mRNA complexation and as such protection of mRNA against enzymatic degradation, we investigated mRNA nanoparticles with a varying N/P ratio (i.e. 'charge ratio'). From gel electrophoresis experiments on DOTAP-cholesterol/ mRNA nanoparticles (results not shown) it can be concluded that complete complexation of the mRNA occurred starting from an N/P ratio of 2.5:1. Hence N/P 2.5:1 mRNA nanoparticles were selected for further experiments. At this charge ratio, the nanoparticles had a mean size of 160 nm and a zeta potential of +50 mV (FIG. 3A).

To predict the stability of the mRNA nanoparticles in vivo and to avoid pre-mature release of the mRNA upon parental injection of the complexes, we incubated the mRNA nanoparticles in human serum for 2 h at 37° C. We performed fluorescence fluctuation spectroscopy (FFS) to allow quantitative information about the mRNA complexation to the DOTAP-cholesterol formulation in serum. Briefly, this technique monitors the fluorescent intensity fluctuations of fluorescent molecules in a small volume. These fluorescence fluctuations are due to the diffusion of the fluorescent molecules in and out of the excitation volume. This technique allows in our case to discriminate free fluorescent mRNA (Cy5 labeled) from fluorescent mRNA associated to the liposomes based on fluorescence intensities. This experiment showed an complexation efficiency of Cy5-modified mRNA of 86±9% for the DOTAP-cholesterol lipoplexes after 2h incubation in serum.

Subsequently we measured the extent of mRNA lipoplex aggregation in serum with fluorescence single particle tracking (fSPT). FIG. 3B clearly demonstrates that the mRNA nanoparticles retain their initial size and do not aggregate in serum-containing medium. Interestingly, this indicates that the inclusion of a PEGylated lipid, typically used to prevent aggregation of nanoparticles, is redundant in this liposomal formulation.

3. mRNA Galsomes: DOTAP-Cholesterol Liposomes as Delivery Agent for Nucleoside-Modified mRNA and α-GalCer It is important to note that both nanoparticle cargos, mRNA and α-GalCer, have different requirements regarding their intracellular delivery. mRNA should rapidly escape from the endosomes to allow adequate antigen production. By contrast, α-GalCer must accumulate in late endosomes and lysosomes of DCs, where it is loaded into CD1d molecules and presented to iNKT cells. As such, we first estimated the delivery efficiency for both mRNA and α-GalCer, using DOTAP-cholesterol liposomes as carrier system, and assessed the compatibility between mRNA translation and the α-GalCer presentation process.

Figure 4:
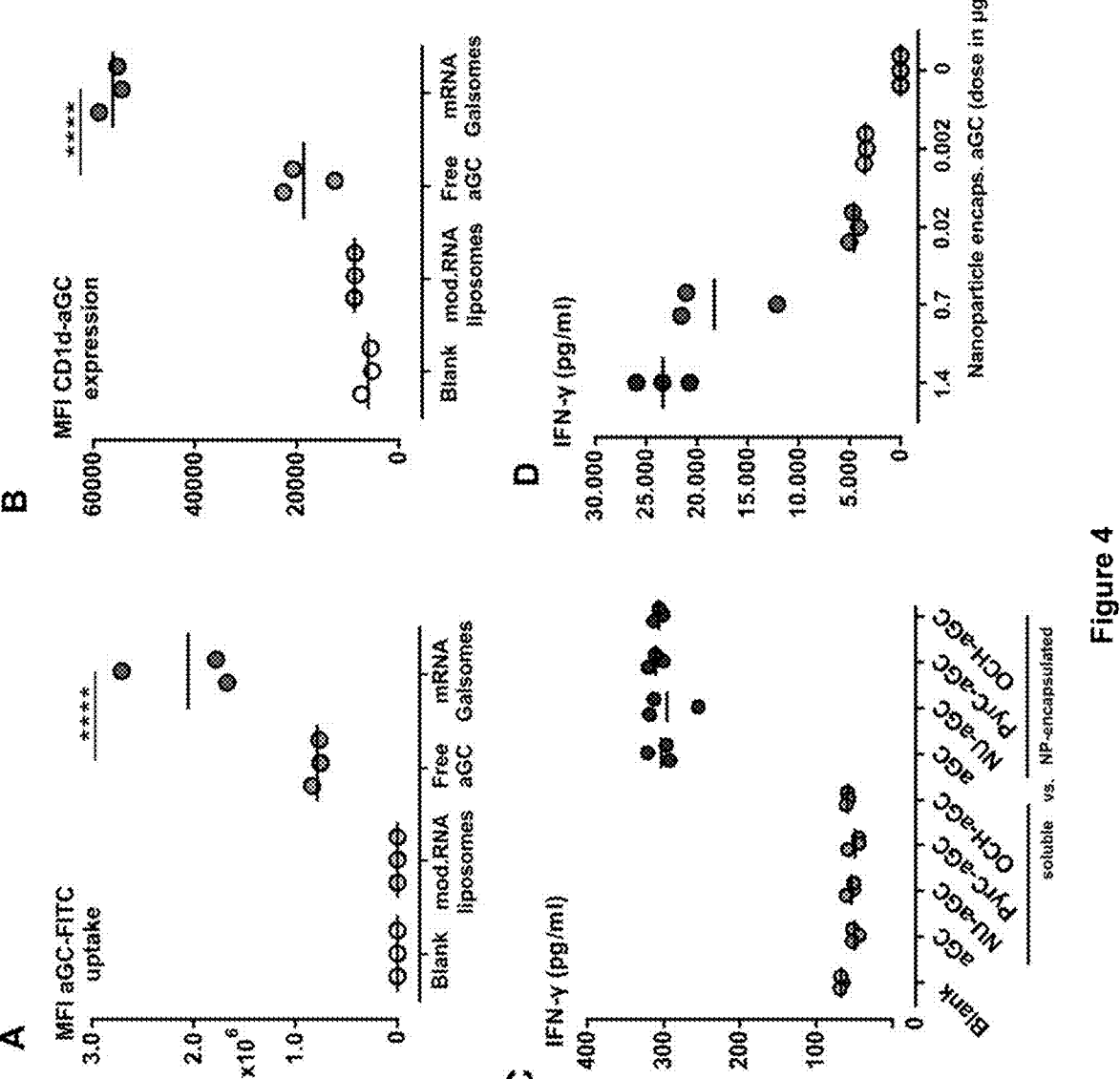
FIG. 4. mRNA Galsomes promote the delivery of α-Gal-Cer to dendritic cells. (A) Enhanced cellular delivery of FITC-labelled α-GalCer formulated in mRNA Galsomes compared to naked α-GalCer, evaluated 24h after incubation with BM-DCs. (B) Enhanced surface presentation of α-Gal-Cer in CD1d complexes by BM-DCs 24h after incubation with α-GalCer in mRNA Galsomes. (panels show representative data (n=3) of three independent experiments). (C) Supernatant of co-cultures (24h) of splenocytes and BM-DCs transfected with nanoparticles packaging different glycolipid antigens, showed higher levels of IFN-γ versus co-cultures with naked α-GalCer, or modified mRNA alone. (D) Dose-response experiment: IFN-γ production in serum of C57Bl/6 mice 12h after i.v. injection of mRNA Galsomes containing decreasing doses of α-GalCer.

To evaluate α-GalCer delivery, bone marrow-derived DCs (BM-DCs) were incubated either with free α-GalCer or mRNA Galsomes (containing equal doses of α-GalCer). When using FITC-labelled α-GalCer, it was clear that the intracellular delivery of α-GalCer was doubled by the delivery via mRNA Galsomes (FIG. 4A). This also translated in an enhanced presentation of α-GalCer in CD1d: we observed a ~3-fold increase in the presentation of α-GalCer via CD1d complexes compared to the soluble α-GalCer format (FIG. 4B). When we cultured BM-DCs together with splenocytes, we could demonstrate a 4-to-5 times higher production of IFN-γ in co-cultures with cells treated with mRNA Galsomes. Interestingly, similar effects were observed when different α-GalCer analogs were packaged inside the nanoparticles (FIG. 4C).

To determine the potency of mRNA Galsomes to initiate an immune response in vivo, we performed a dose-response study by injecting mice intravenously with mRNA Galsomes containing a fixed dose of 10 μg mRNA and decreasing doses of α-GalCer (FIG. 4D). Twelve hours post-injection, iNKT cell activation was measured indirectly by the production of IFN-γ in serum. When injecting mRNA Galsomes containing 1.4 μg α-GalCer, a dose which corresponds to the amount of α-GalCer which is routinely administered systemically in mice, levels of IFN-γ up to 25.000 pg ml$^{-1}$ could be detected in serum [26]. Although this indicates that mRNA Galsomes are very potent to induce immunity, this coincided with splenomegaly in all of the animals. However, the levels of IFN-γ could easily be refined by dose adjustments of α-GalCer. Importantly, when drastically lower doses were used, down to 20 ng α-GalCer per mouse (or 0.015 mol % of the total amount of lipids in the nanoparticle), this still resulted in high levels of IFN-γ (~4000 pg ml$^{-1}$), but without any signs of acute toxicity. Therefore, we used mRNA Galsomes packaging 20 ng of α-GalCer for further experiments.

Figure 5:
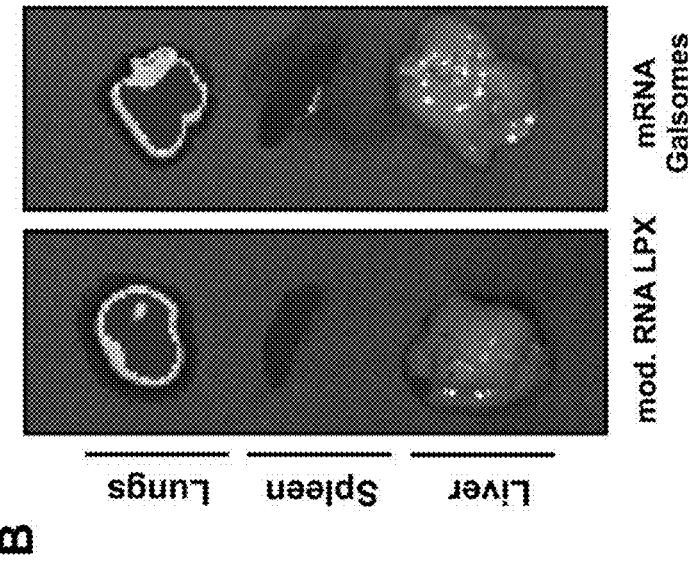
FIG. 5. Systemic administration of mRNA Galsomes results in efficient mRNA transfection in lungs and spleen. (A) Whole-body expression levels of fLuc mRNA in C57Bl/6 mice 6h after i.v. injection of nanoparticles containing different cargos; unmodified-, nucleoside-modified- or nucleoside-modified mRNA nanoparticles formulated with α-GalCer (n=6-7, pooled from two independent experiments) (B) Representative bioluminescence images of isolated organs (lungs, spleen and liver).
Figure 5:
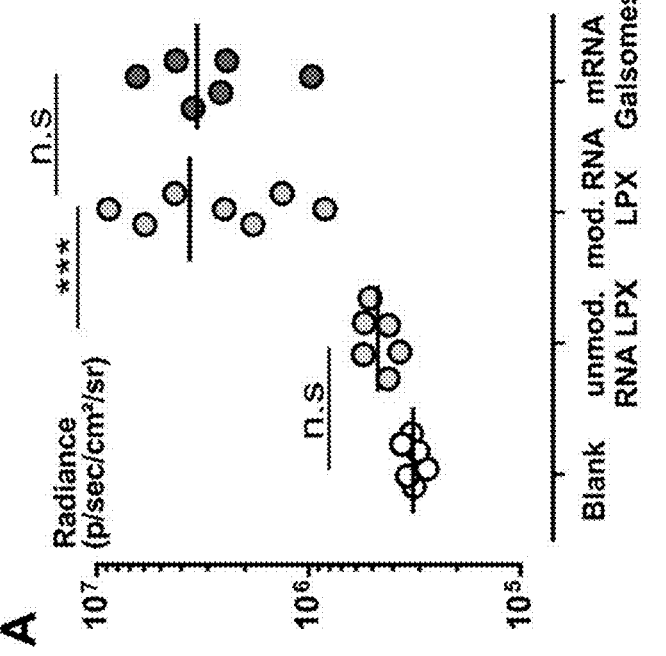
Figure 6:
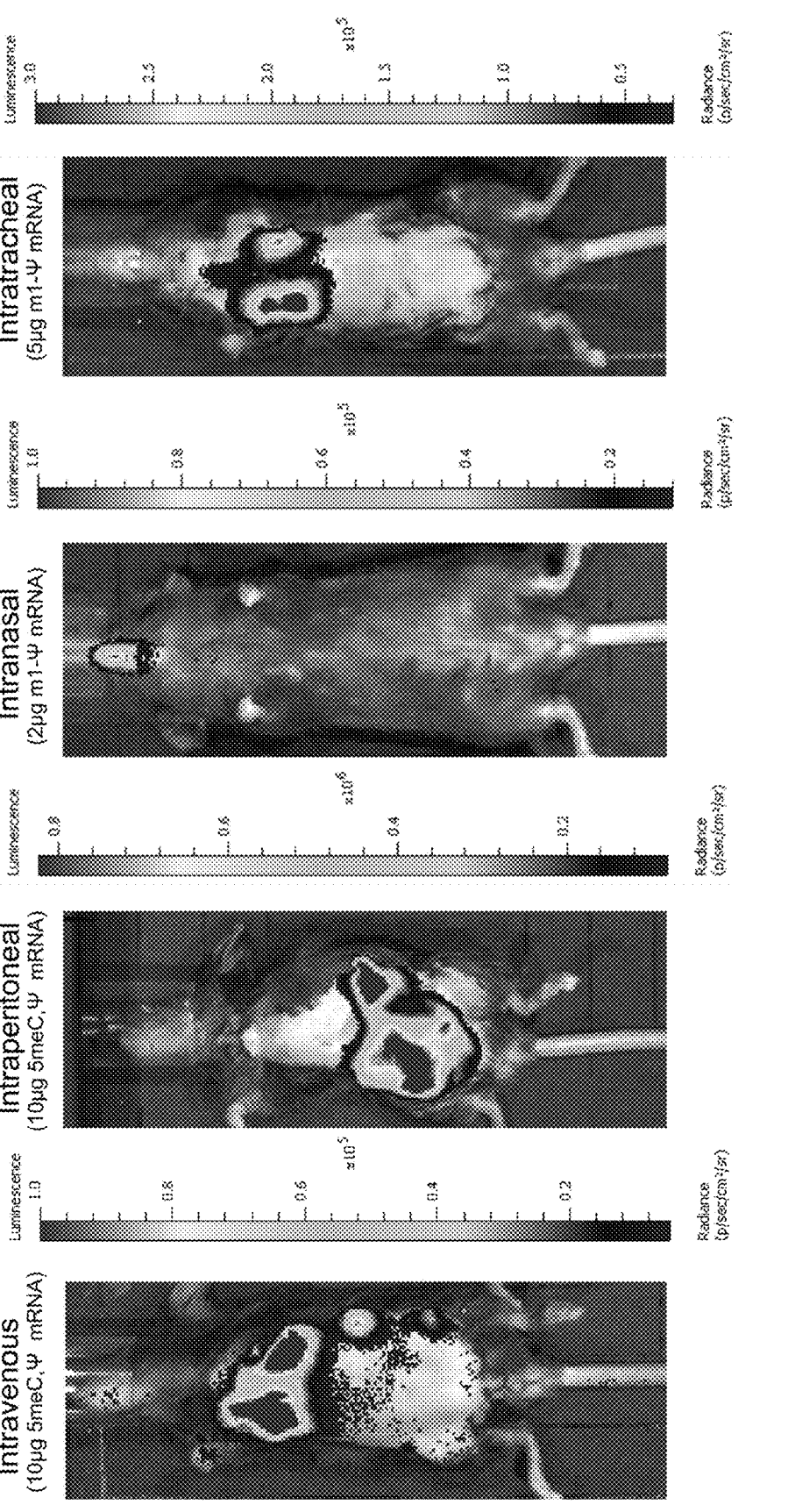
FIG. 6. C57Bl/6 mice were administered with DOTAP-cholesterol nanoparticles containing fLuc encoding mRNA via different administration routes; intravenous, intraperitoneal, intranasal or intratracheal administration. Depending on the administration route different mRNA doses and/or mRNA modifications were used, as depicted in the figure. Figure shows representative bioluminescence images of mice 6h after administration of the mRNA nanoparticles.

Previous attempts where mRNA was combined with other adjuvants have raised compatibility issues, since DC maturation can prematurely abrogate cellular uptake mechanisms (e.g. macropinocytosis) or potentially induce anti-RNA defense mechanisms (e.g. type I IFN signalling) leading to fast mRNA degradation [19, 27]. For these reasons we investigated the impact of α-GalCer inclusion on mRNA translation. Mice were injected intravenously with nanoparticles encapsulating different cargos: nucleoside-modified mRNA alone, nucleoside-modified mRNA combined with α-GalCer or unmodified mRNA (immunogenic) encoding firefly luciferase (fLuc). Bioluminescence was evaluated 6h later. FIGS. 5A-B demonstrate that incorporation of α-GalCer did not interfere with the translation of mRNA in lungs and spleen. As expected, unmodified fLuc mRNA nanoparticles display significantly lower expression levels, which results from their lower intracellular stability, as well as from type I IFN-mediated antiviral pathways programmed to degrade and avoid the translation of mRNA [27]. Note that the nanoparticles of the invention can also be used for the delivery of mRNA via other administration routes, such as intraperitoneal, intranasal or intratracheal administration (FIG. 6). Together, these results indicate that co-packaging of nucleoside-modified mRNA and α-GalCer improves α-GalCer delivery and presentation, without affecting the mRNA expression levels.

Figure 7:
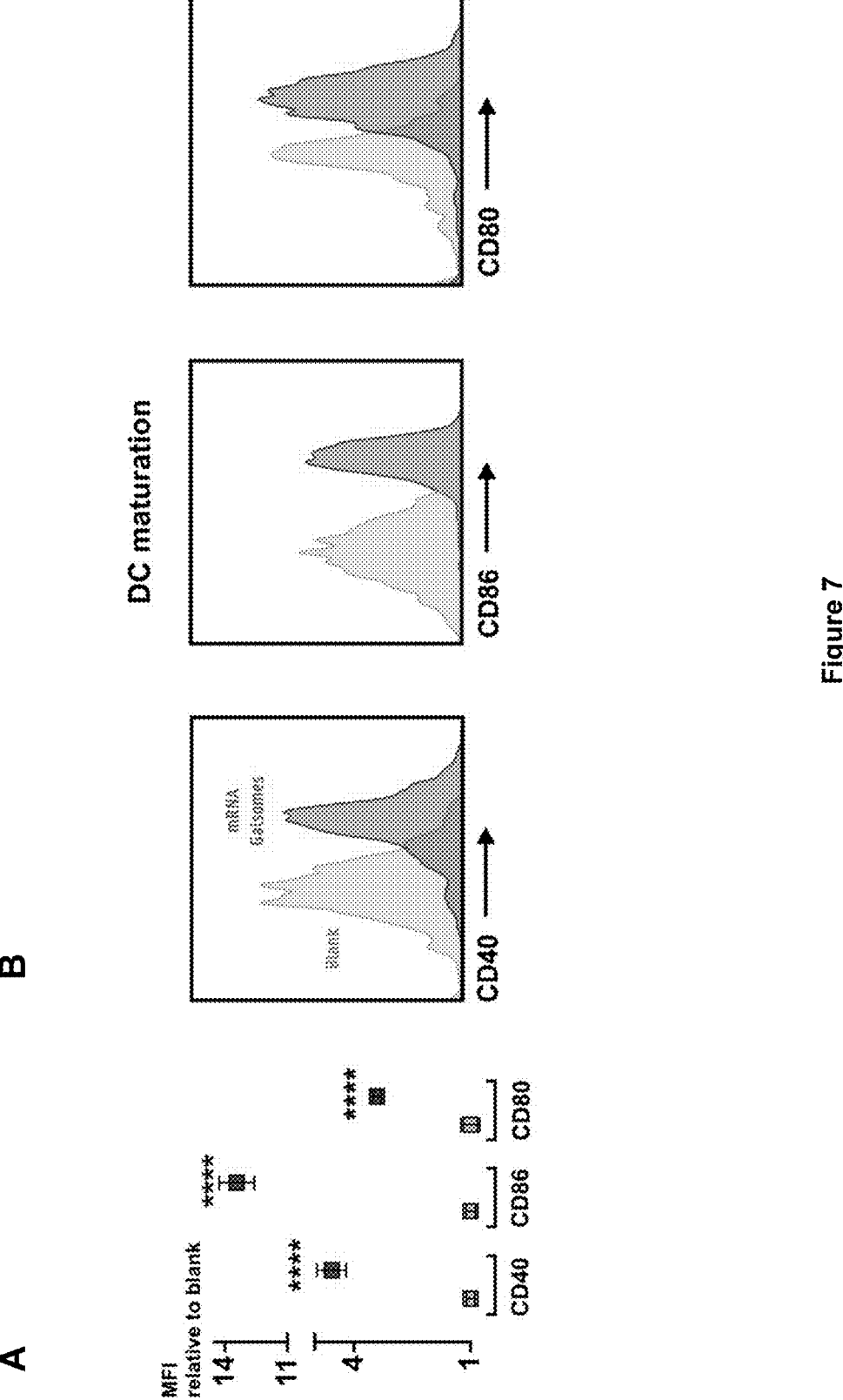
FIG. 7. mRNA Galsomes containing low doses of α-GalCer (20 ng) induce the maturation of dendritic cells in vivo (A) Splenic DCs (CD11c$^{high}$ population) showed an increase in the expression of the activation markers CD40, CD86 and CD80 (expressed as a fold change in MFI) 24h after administration of mRNA Galsomes (n=4). (B) Representative histograms of CD40, CD86 and CD80 expression.

4. mRNA Galsomes Mediate Strong Adjuvant Effects and Activate Dendritic Cells In Vivo Immune activation by α-GalCer is an indirect phenomenon: DCs that present α-GalCer in CD1d will stimulate iNKT cells, which, in turn, cause phenotypic maturation of DCs by CD40-CD40-ligand interaction. To assess if this is also the case for mRNA Galsomes, especially with the low (20 ng) α-GalCer doses used, we investigated the maturation status of splenic DCs 24h after particle injection (FIG. 7A-B). We could observe a strong and significant up-regulation of the activation markers CD40, CD80 and CD86 on splenic DCs, relative to untreated mice. Importantly, DC maturation was not observed when mRNA Galsomes were added to BM-DC cultures in the absence of iNKT cells, indicating that this maturation effect was mediated by the ligation with iNKT cells.

Figure 8:
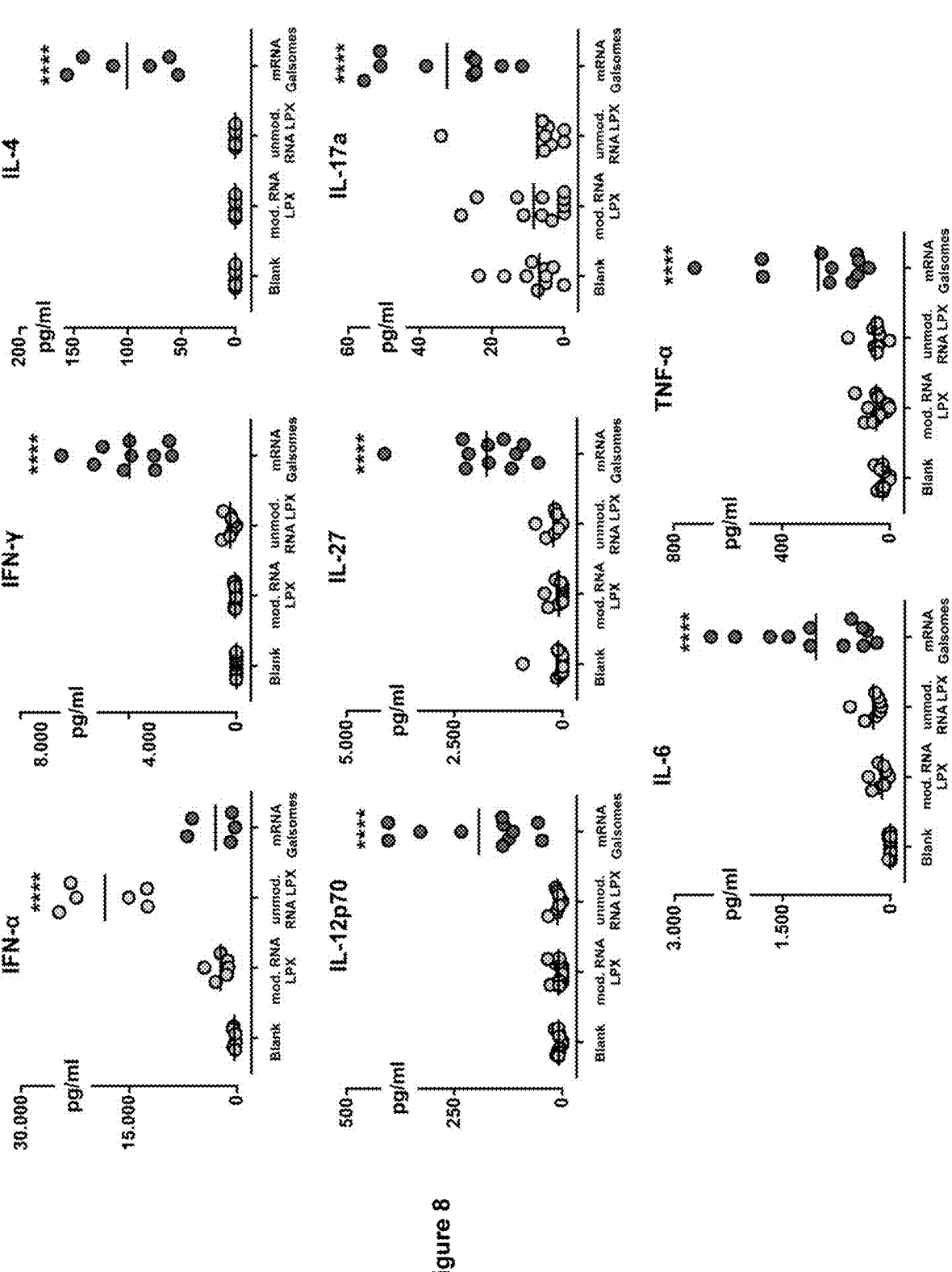
FIG. 8. mRNA Galsomes containing low doses of α-GalCer (20 ng) stimulate the release of immunostimulatory cytokines. Serum samples were collected at 6h post-injection and screened for the release of inflammatory cytokines: while unmodified mRNA nanoparticles trigger the production of IFN-α, mRNA Galsomes induce distinct cytokine responses, including IFN-γ, IL-4, IL-12p70, IL-27, IL-17a, IL-6 and TNF-α. Data are pooled from at least two independent experiments.

To investigate the width of the immune response, a broad screening of inflammatory cytokines was performed in blood of animals 6h after vaccination (FIG. 8). As expected, where unmodified mRNA nanoparticles induced a strong release of IFN-α, this was not the case with nucleoside-modified mRNA nanoparticles (with or without α-GalCer). By contrast, mRNA Galsomes induced a pronounced production of IFN-γ and IL-4. What is more, in the group receiving mRNA Galsomes, we could also detect the presence of T cell-stimulating cytokines, such as IL-12p70 and IL-27, and elevated levels of IL-6, TNFα and IL-17a.

Importantly, this broad spectrum of cytokines did not induce visible toxicity symptoms, no pathological changes were identified in H&E stained organ sections of lungs, spleen and liver, and normal levels of ALT activity were measured.

5. mRNA Galsomes as Pluripotent Inducers of Immunity

One could expect that the increased mRNA expression levels combined with strong DC maturation, and the production of CTL-inducing cytokines such as IL-12p70, hold potential for mRNA Galsomes to compete with type I IFN-dependent mRNA vaccines. In addition to T cell-mediated immunity, the combination with α-GalCer could also offer the advantage of activating both iNKT- and NK cells shaping a broader and potentially synergistic antitumor immunity.

Figure 9:
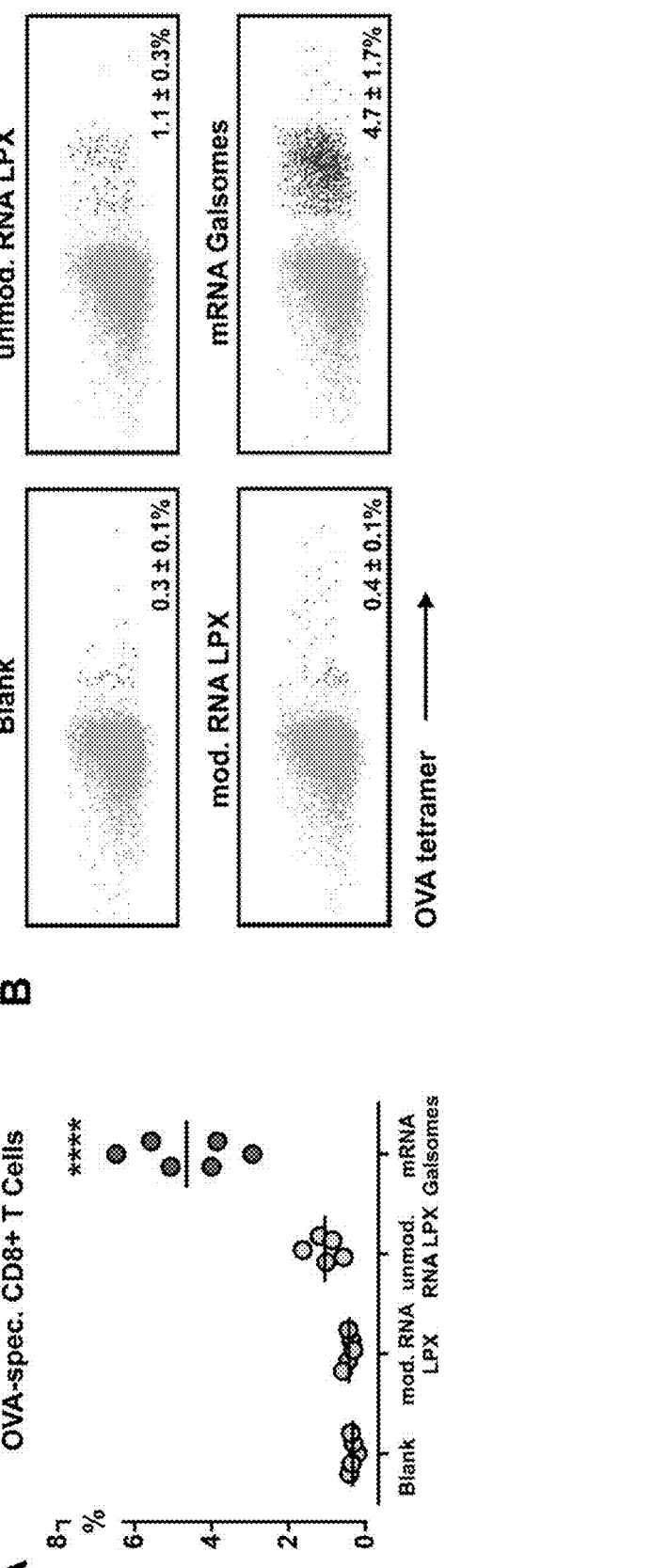
FIG. 9. mRNA Galsomes mediate superior antigen-specific CD8$^+$ T cells responses, over nanoparticles packaged with unmodified mRNA. (A) α-GalCer strongly mediates the induction of antigen-specific CD8$^+$ T cell responses. Mice were immunized with OVA mRNA nanoparticles. 6 days later, percentages of OVA-specific CD8$^+$ T cells in spleen were measured using an H-2 kb OVA tetramer staining. (B) Representative flow cytometry scatter plots of OVA specific CD8$^+$ T cells.

To evaluate these multiple effector responses, animals were immunized with mRNA encoding chicken ovalbumin (OVA) as a model antigen. Six days after immunization, cell numbers of OVA-specific CTLs were measured in isolated spleens (FIG. 9). Interestingly, we observed that mRNA Galsomes generated 4 to 5 times higher levels of OVA-specific CTLs compared to mice treated with "golden standard" unmodified OVA mRNA nanoparticles.

Figure 10:
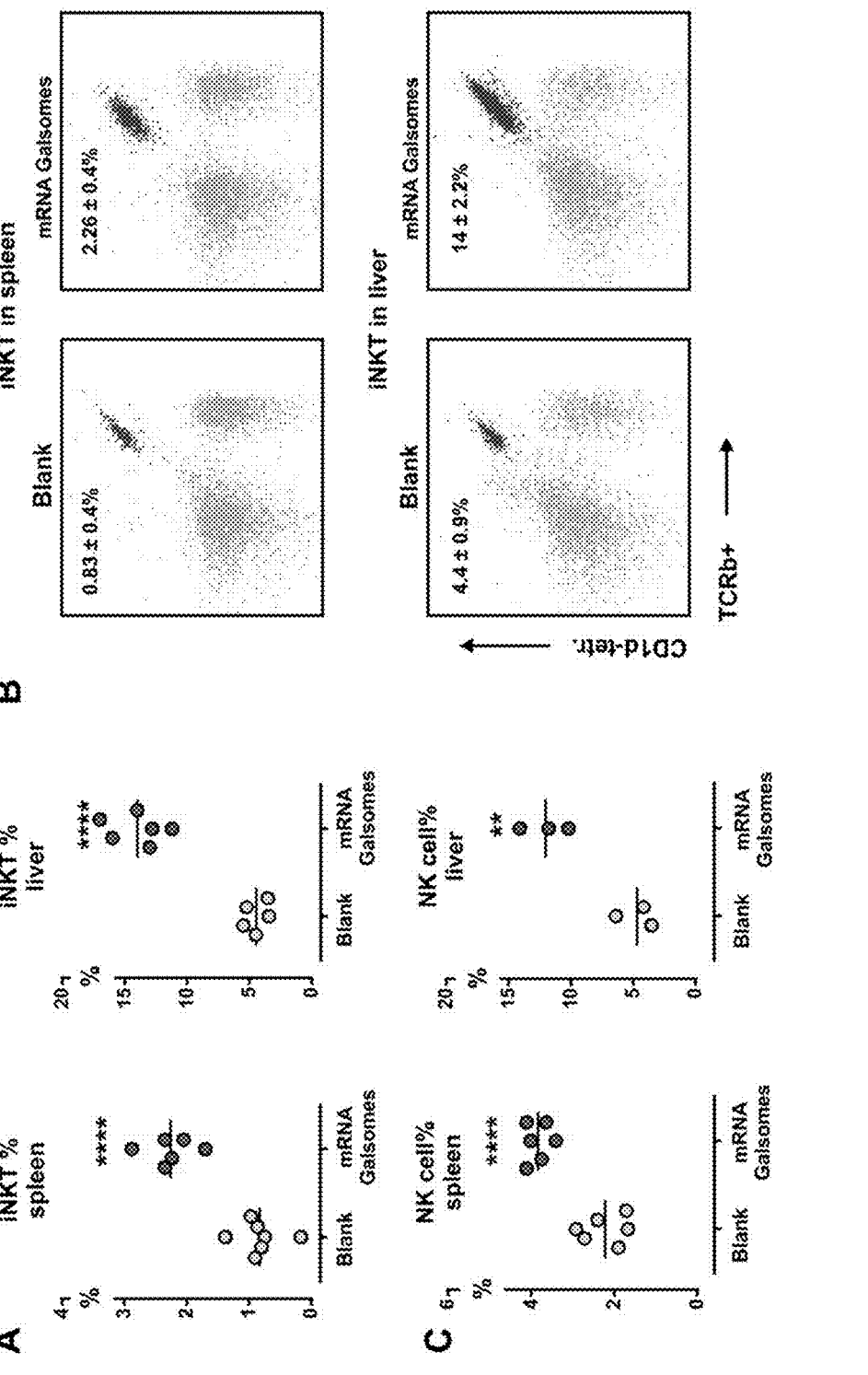
FIG. 10. Systemic administration of mRNA Galsomes results in the expansion of iNKT and NK cells. (A) Three days post-injection of mRNA Galsomes, spleen and liver displayed expanded iNKT cell numbers compared to untreated mice. (B) Representative flow plots of iNKT cells in spleen and liver (TCRβ$^+$, mCD1d PBS-57$^+$ cells). (C) Down-stream activation of NK cells (CD3$^-$, NK1.1$^+$ cells). The data in this figure (n=6) are pooled from two independent experiments.

To evaluate the proliferation of iNKT- and down-stream NK cell responses, spleen and liver were isolated 3 days after vaccination. Corresponding to the cytokine responses (FIG. 8), we observed an increased proliferation of iNKT cells, from 0.8 to 2.3% in spleen and 4.4 to 14% in liver (FIG. 10A-B). Accordingly, mRNA Galsomes also mediated the proliferation of NK cells as their levels increased from 2.2 to 3.8% and 4.7 to 12%, in spleen and liver, respectively. (FIG. 10C).

6. Therapeutic Efficacy of mRNA Galsomes in E.G7-OVA Lymphoma- and B16-OVA Melanoma Models To assess the potential of mRNA Galsomes in a therapeutic vaccination study, mice were subcutaneously inoculated with OVA-expressing E.G7 lymphoma cells or B16-OVA melanoma cells and vaccinated when tumors were palpable at day 8 with mRNA encoding OVA.

Figure 11:
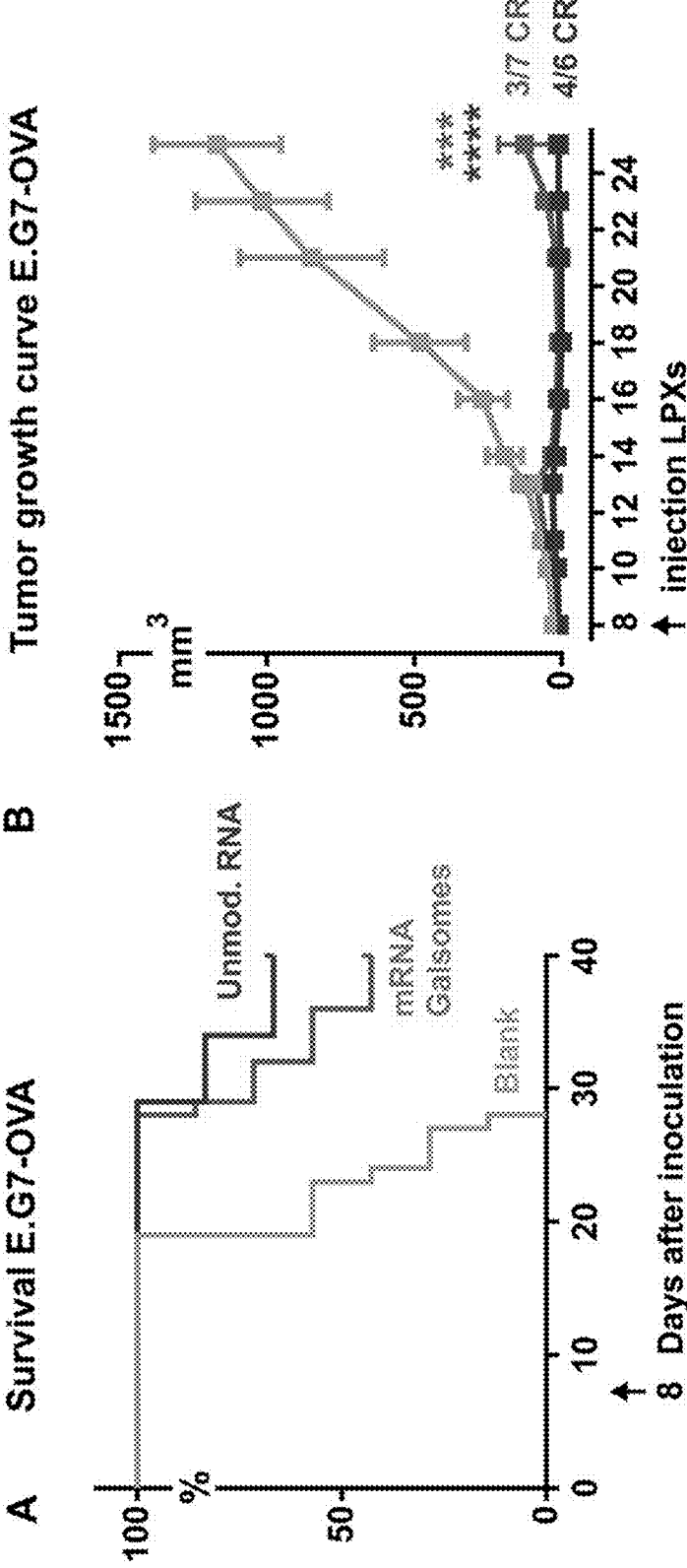
FIG. 11. Therapeutic vaccination with OVA mRNA Galsomes or unmodified mRNA nanoparticles in E.G7-OVA lymphoma. Mice were subcutaneously inoculated with E.G7-OVA lymphoma cells (3×10$^5$ cells). E.G7-OVA tumor bearing mice were vaccinated on day 8 when tumors were clearly visible. Graphs show Kaplan-Meier survival curves and the respective tumor growth curves (A and B) as a function of time for an untreated control group, and for mice treated with OVA mRNA Galsomes or unmodified OVA mRNA nanoparticles (n=7-8).

E.G7-OVA bearing mice were treated with a single administration of either mRNA Galsomes or nanoparticles containing unmodified mRNA, in order to differentiate between the therapeutic potential of nanoparticles that evoke immunity based on iNKT cell activation or a type I IFN response, respectively. First of all, both therapies resulted in a significant slow-down in tumor progression, relative to untreated mice (FIG. 11A-B). Overall, mice treated with unmodified mRNA nanoparticles, showed complete tumor regression in 4/6 animals, and treatment with mRNA Galsomes resulted in complete tumor regression in 3/7 animals.

Figure 12:
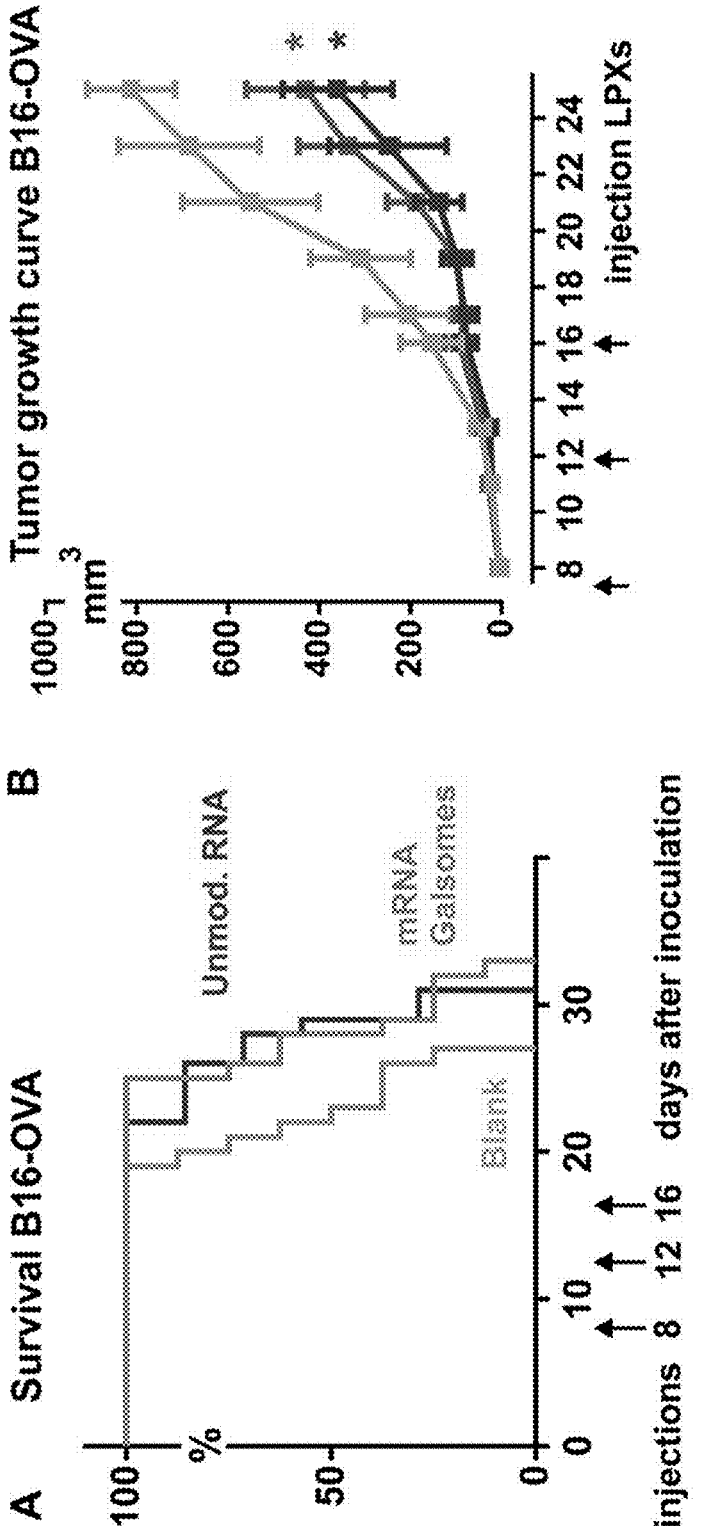
FIG. 12. Therapeutic vaccination with OVA mRNA Galsomes or unmodified mRNA nanoparticles in B16-OVA melanoma model. Mice were subcutaneously inoculated with B16-OVA lymphoma cells (3×10$^5$ cells). B16-OVA bearing mice received three vaccinations on day 8, day 12 and day 16. Graphs show Kaplan-Meier survival curves and the respective tumor growth curves (A and B) as a function of time for an untreated control group, and for mice treated with OVA mRNA Galsomes or unmodified OVA mRNA nanoparticles (n=7-8).

In a more aggressive B16-OVA melanoma model, animals received 3 administrations of either mRNA Galsomes or unmodified mRNA nanoparticles on day 8, day 12 and day 16 after tumor inoculation. Although we observed a delay of tumor outgrowth, there was only a modest prolongation of survival for mice treated with mRNA Galsomes or unmodified mRNA nanoparticles, with median survival of 28 days and 29 days, compared to 22.5 days for untreated animals (FIG. 12A-B). In addition, we noticed that multiple administrations could not efficiently boost or prolong the antitumor responses. This also occurred in the E.G7-OVA model, where a second (boost) vaccination did not result in better control of tumor outgrowth.

7. mRNA Galsomes Promote the Tumor Infiltration of CTLs, iNKT Cells and NK Cells, but Immune Surveillance is Hampered by the Expression of PD-L1

Figure 13:
FIG. 13. Therapeutic vaccination with mRNA Galsomes results in tumor infiltration of effector cells. B16-OVA bearing mice which received two vaccinations were sacrificed on day 14 and evaluated for infiltration CD8$^+$ T cells (A) and OVA-specific CD8$^+$ T cells (B), iNKT cells (C) and NK cells (D).
Figure 14:
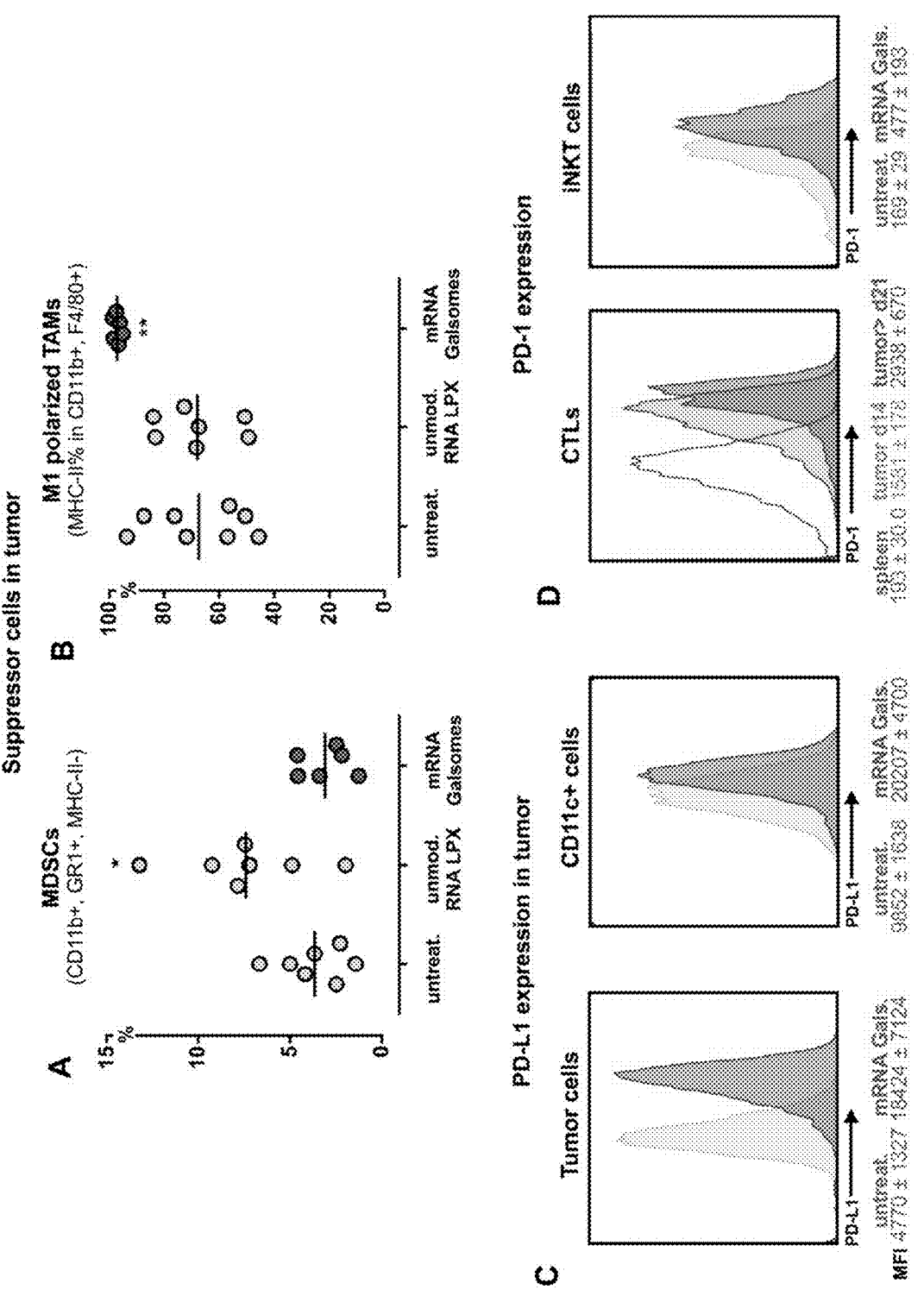
FIG. 14. Therapeutic vaccination with mRNA Galsomes positively affects suppressive myeloid cells in B16 OVA melanoma, but activates the PD-1/PD-L1 pathway. (A) Presence of MDSC (CD11 b$^+$, GR1$^+$, MHC-II$^-$) and (B) M1 polarized TAMs (CD11b$^+$, F4/80$^+$, MHC-II$^+$) in tumor site (n=8, pooled from two independent experiments). (C) mRNA Galsomes induced PD-L1 expression on tumor cells (CD45$^-$) and APCs (CD45$^+$, CD11c$^+$) (n=5). (D) Tumor-infiltrating CD8$^+$ T cells were evaluated for the expression of PD-1 at day 14 (two days after boost) (n=6-8, pooled from two experiments) or at later time points between day 21-33, when the tumor volume had reached 1000 mm$^3$ (n=5). CD8$^+$ T cells displayed higher surface expression levels of PD-1 at the tumor site. Activated iNKT cells in spleen exhibited an increased expression of PD-1, measured 3 days after initial challenge with mRNA Galsomes (n=8, pooled from two experiments).

Since complete control of tumor outgrowth was not achieved, we aimed to investigate which immune suppressive mechanisms might be at play to counteract the evoked antitumor immunity by mRNA Galsomes or unmodified mRNA nanoparticles. Therefore, experiments were performed where B16-OVA bearing mice were sacrificed 2 days after a second nanoparticle administration (day 14), and a detailed analysis of the tumor immune microenvironment was performed. Tumor and spleen were screened for effector responses and/or suppressive mechanisms that could impact the therapeutic outcome. The most important findings are shown in FIG. 13-14.

First of all, animals treated with mRNA Galsomes exhibited up to 5 times higher levels of tumor infiltrating CTLs, whereas CTL presence at the tumor site merely doubled after vaccination with unmodified mRNA nanoparticles compared to the untreated group (FIG. 13A). Likewise, vaccinations with mRNA Galsomes resulted in 6 to 7 times higher numbers of CTLs specific for OVA (10% of viable cells in tumor, as determined by SIINFEKL-H2Kb tetramer staining) compared to unmodified mRNA treated animals, while almost no (<0.04%) OVA-specific CTLs were detected in the tumors of the untreated animals (FIG. 13B). In addition, we detected a 4-fold increase in iNKT cell numbers in the tumors of mice treated with mRNA Galsomes, compared to the other groups (FIG. 13C). For both treatments, increased levels of tumor-infiltrating NK cells were observed, with ±13% NK cells for mRNA Galsomes and ±11% NK cells for unmodified mRNA nanoparticles compared to untreated mice with only ±5% NK cells (FIG. 13D).

By analysing the tumor site for suppressive immune cells, we found that the delivery of unmodified mRNA resulted in a 2-fold increase in MDSCs (CD11b$^+$, GR1$^+$, MHC-II$^-$ cells) compared to untreated controls. Interestingly, this rise in MDSC levels was not observed in animals treated with mRNA Galsomes (FIG. 14A). Furthermore, we noticed that almost all TAMs (CD11b$^+$, F4/80$^+$ cells) in the mRNA Galsome-group displayed a pro-inflammatory M1-like phenotype, marked by increased levels of MHC-II (FIG. 14B).

While vaccination with mRNA Galsomes resulted in "hot" T cell-infiltrated tumors, we investigated whether immune suppression via the PD-1/PD-L1 axis could be involved in countering the vaccine-induced immune response [23]. Indeed, tumors of mice treated with mRNA Galsomes exhibited a ~4-fold increase in PD-L1 expression, compared to tumors of untreated animals. Similar effects were observed for APCs within tumors, which were subject to a ~2-fold up-regulation of PD-L1 expression compared to controls (FIG. 14C). In addition, various tumor-infiltrating T cell subsets, including CD8$^+$ T cells, OVA-specific CTLs and CD4$^+$ T cells exhibited an up-regulation of PD-1 expression, which increased over time (FIG. 14D). It should be noted that these effects occurred regardless of the type of mRNA nanoparticle: PD-1 up-regulation was measured in similar amounts for both mRNA Galsomes and unmodified mRNA nanoparticles. Importantly, we also observed significantly elevated PD-1 expression in activated iNKT cells after the initial challenge with mRNA Galsomes (FIG. 14D). This is in line with the limited boost-effect we observed upon multiple injections of the mRNA Galsomes (FIGS. 11-12) and matches previous reports where inhibitory signals via the PD-1/PDL-1 pathway were suggested to play a role in the loss of responsiveness to subsequent α-GalCer stimulations after (over-) stimulation.

Taken together, these findings demonstrate that the inhibitory PD-1/PD-L1 immune checkpoint axis is involved in the suppression of CTLs, and that it could potentially explain the limited responsiveness of iNKT cells to a second (boost) vaccination, thus limiting antitumor immunity.

8. Anti-PD-L1 Checkpoint Blocking Antibodies Synergize With the Antitumor Effects of mRNA Galsomes The previous data suggest that increased PD-1/PD-L1 signaling limits antitumor immunity by paralyzing T-cell responses and inducing iNKT cell anergy. This provides a rationale to investigate the therapeutic combination of mRNA Galsome vaccination with anti-PD-L1 immune checkpoint inhibition.

Figure 15:
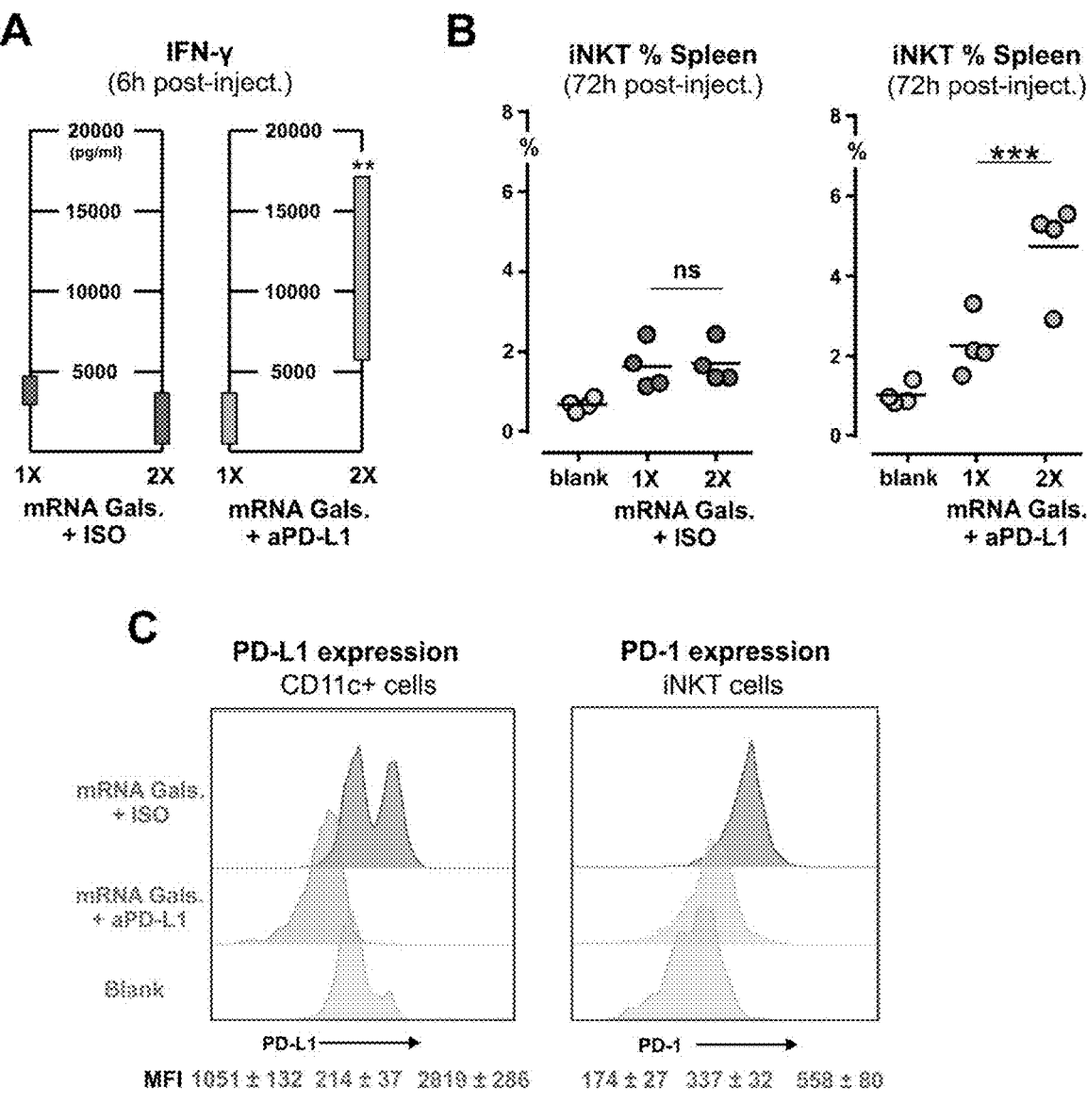
FIG. 15. Checkpoint inhibition with anti-PD-L1 antibodies prevents the induction of iNKT anergy after stimulation with mRNA Galsomes. For the evaluation of iNKT anergy, naïve mice received two subsequent exposures of mRNA Galsomes, with 5 days between the first and second administration. (A) Graph showing the production of IFN-γ in serum, collected 6h after the first- and second administration of mRNA Galsomes, combined with either isotype- or anti-PD-L1 antibodies. Bars display mean±SD (n=4). (B) Percentages of iNKT cells (TCRβ+, mCD1d PBS-57+ cells) among splenocytes, measured 3 days after each vaccination. (C) PD-L1 expression on splenic DCs (CD11c+ cells) and PD-1 expression on iNKT cells, measured 6h after the first treatment and 3 days after the second treatment, respectively (n=4).

To first investigate the problem of iNKT anergy in more detail, naïve mice were vaccinated twice with mRNA Galsomes with a 5 day interval. At respectively 6h and 3 days after each administration, we evaluated the cytokine release and iNKT activation. As shown in FIG. 15A, IFN-γ levels measured after the second exposure were only half of the levels measured after the first administration. In addition, we could observe a shift towards the production of Th2 polarized cytokines after successive administrations, as higher levels of IL-4 and IL-10 were measured. Finally, we noticed that a boost-vaccination with mRNA Galsomes did not further augment iNKT cell numbers, confirming the induction of a hypo-responsive state of iNKT cells. In shear contrast, when mice were simultaneously vaccinated and injected with anti-PD-L1 antibodies, IFN-γ production rose up to 4 times higher upon the second vaccination, compared to the initial challenge. Along the same line, the combination with anti-PD-L1 antibodies further boosted the expansion of iNKT cells, as a second administration doubled the number of splenic iNKT cells (2.25±0.7 versus 4.73±1.2%, FIG. 15B). To further investigate the role of PD-1/PD-L1 signaling, we measured the PD-L1 expression of splenic DCs and PD-1 expression of activated iNKT cells. Similar to other reports, we observed a large fraction of DCs that rapidly up-regulated the expression of PD-L1 in animals treated with isotype controls, which could be fully eliminated by the concomitant delivery of anti-PD-L1 antibodies (FIG. 15C) [28, 29]. In addition, repeated activation of iNKT cells by the mRNA Galsomes/checkpoint combination strategy was feasible, as the PD-1 levels were reduced by half compared to iNKT cells of mice that merely received a single vaccination with mRNA Galsomes alone (FIG. 15C).

Figure 16:
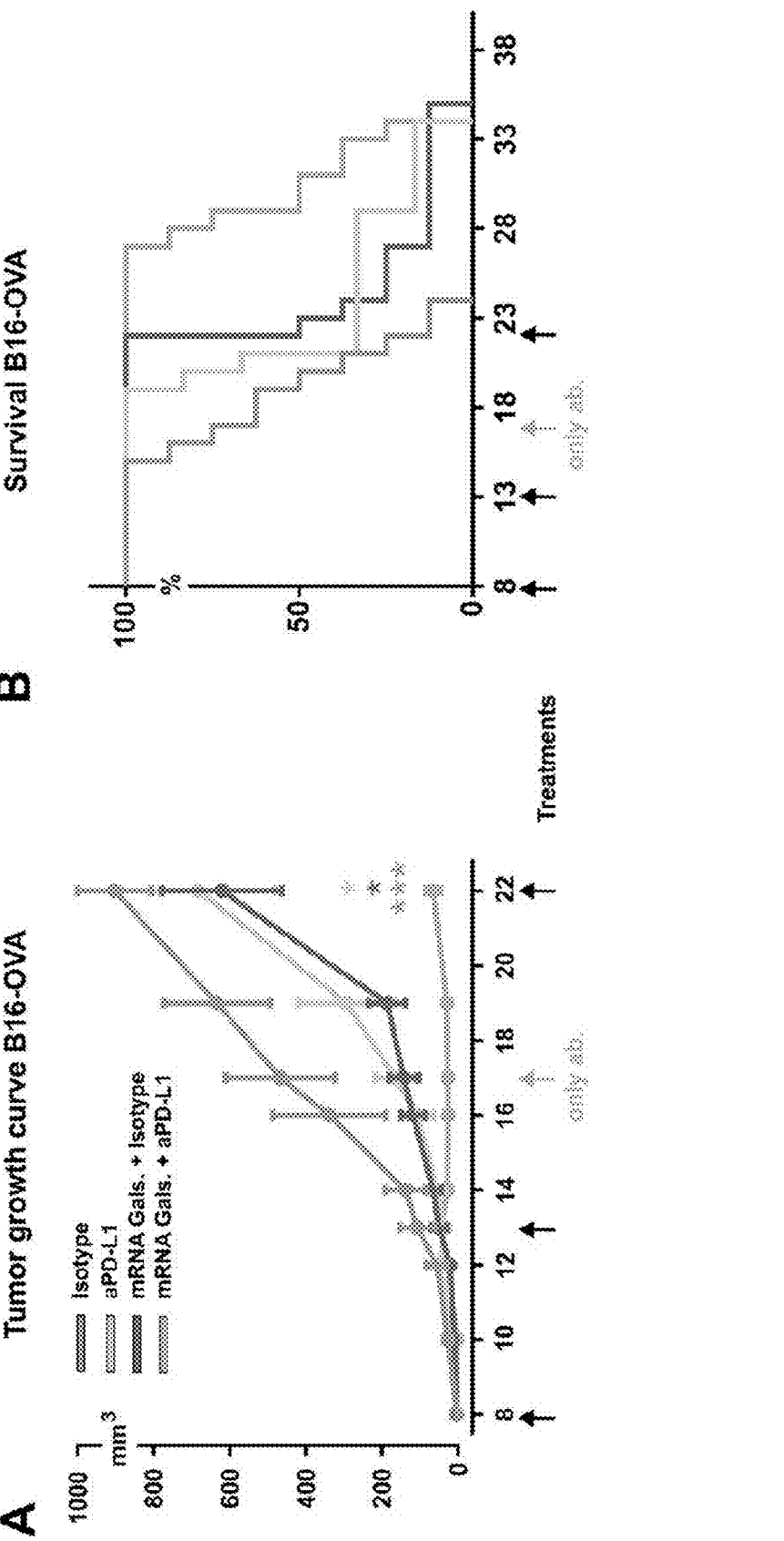
FIG. 16. mRNA Galsomes combined with anti-PD-L1 antibodies improves therapeutic outcome in B16-OVA melanoma bearing mice. Mice were subcutaneously inoculated with B16-OVA melanoma cells ($5 \times 10^5$ cells), and vaccinated on day 8 when tumors were clearly visible. For this, B16-OVA bearing mice were i.p. administered with 100 µg of rat IgG2b antibodies (isotype control) or anti-PD-L1 antibodies in monotherapy, or in combination therapy with mRNA Galsomes. Graph (A) shows average tumor growth curves and (B) Kaplan-Meier survival curves for respective treatments, demonstrating synergistic effects between anti-PD-L1 antibodies and mRNA Galsomes (n=6-8). The arrows indicates the days of treatment.

To evaluate if the above-mentioned effects of the combination therapy could also be translated into an improved therapeutic outcome, B16-OVA bearing mice were vaccinated with mRNA Galsomes combined with intraperitoneal administrations of either anti-PD-L1 antibodies or isotype control antibodies. Monotherapy of anti-PD-L1- or isotype antibodies were used as additional controls. The results in FIG. 16 show that by the time of the last vaccination (day 22), the average tumor volume of mice treated with a combination of mRNA Galsomes and checkpoint blocking antibodies, remained limited to 59±46 mm³. By contrast, in all other groups, tumors had already grown up to 10 times larger. This also translated into a significant increase in median survival. Mice receiving monotherapy of anti-PD-L1 antibodies or mRNA Galsomes had reached their median survival at day 21 and 22.5, respectively, which is not significantly later than animals in the control group where only isotype control antibodies were injected (median survival of 19 days). The combination treatment significantly prolonged median survival to 30 days, indicating a synergistic effect between both treatment strategies.

Figure 17:
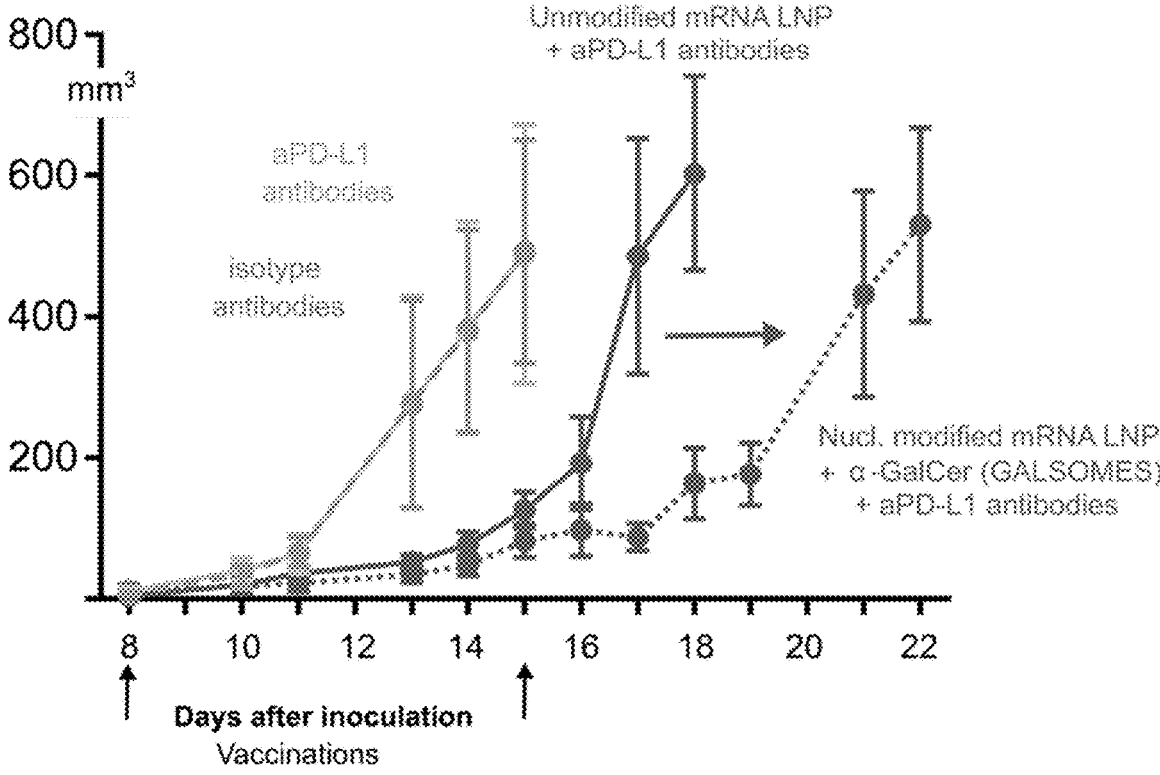
FIG. 17. Combination therapy of anti-PD-L1 antibodies with mRNA Galsomes or unmodified mRNA nanoparticles encoding a relevant tumor antigen TRP-2. Mice were subcutaneously inoculated with B16F0 melanoma cells ($5 \times 10^5$ cells), and vaccinated on day 8 when tumors were clearly visible. B16F0-bearing mice were i.p. administered with 100 µg of a rat IgG2b antibody (isotype control) or anti-PD-L1 antibody in monotherapy or in combination therapy with either Galsomes or unmodified mRNA nanoparticles containing TRP-2 encoding mRNA. Graph shows average tumor growth curves for respective treatments (n=6). The arrows indicates the days of treatment.

Next, we investigated whether similar antitumor responses could be obtained targeting a naturally expressed tyrosinase related protein 2 (TRP-2) tumor antigen in a B16F0 melanoma model. More specifically, B16F0 bearing mice received vaccinations of either mRNA Galsomes or unmodified mRNA nanoparticles now containing mRNA encoding TRP-2 with a combination of anti-PD-L1 checkpoint therapy (FIG. 17). When both mRNA platforms in combination with the checkpoint therapy were evaluated in a head-to-head comparison, we could now observe superior antitumor effects with the mRNA Galsome formulation over the unmodified mRNA nanoparticles, demonstrated by a median survival of 24 days versus 18 days, respectively. Again, B16F0 bearing mice were unresponsive to monotherapy of PD-L1 checkpoint inhibition with animals that received isotype control antibodies or anti-PD-L1 antibodies both reaching their median survival at day 15.

Overall, it was clearly shown that the therapeutic potential of mRNA Galsomes can be strengthened by rationally combining with PD-L1 checkpoint inhibition. This checkpoint blockage (1) prevents the induction of iNKT anergy allowing multiple vaccination rounds, and (2) avoids adaptive resistance mechanisms at the tumor site prolonging antitumor effects in the B16-OVA- or B16F0 melanoma model. Moreover, mRNA Galsomes can obtain superior antitumor responses over the state-of-the-art unmodified mRNA nanoparticles since they can shift the tumor microenvironment towards a more pro-inflammatory phenotype, and they showed prolonged survival in combination with PD-L1 checkpoint inhibition as e.g. demonstrated in the B16F0 melanoma model targeting TRP-2.

9. mRNA Galsomes Formulated With Functional Derivatives of α-GalCer.

In addition, we tested the therapeutic potential of mRNA Galsomes formulated with α-GalCer analogs, which are specifically synthesized to increase or reduce the stability of the glycolipid within the CD1d complex. Three functional derivatives were selected: (1) NU-α-GalCer (α-GalCer-6″-(1-naphthyl)urea, (2) PyrC-α-GalCer (α-GalCer-6″-(pyridin-4-yl)carbamate) and (3) (2S,3S,4R)-1-O-(α-D-Galactopyranosyl)-N-tetracosanoyl-2-amino-1,3,4-nonanetriol) (OCH). The NU- and PyrC-analogs have a modification of the galactose moiety with respectively a naphthylurea and pyridine carbamate group resulting in an increased interaction with the CD1d (dendritic cells) or TCR receptor (iNKT cells), respectively. In contrast, OCH is a ceramide-modified analogue with shorter acyl chains and is therefore known to have a weaker affinity for the CD1d receptor.

mRNA Galsomes were prepared with inclusion of either α-GalCer or one of the structural analogs (0.015 mol % of total lipid amount). First, we compared the activity of these mRNA Galsomes to evoke iNKT- and antigen-specific CTL responses in tumor-free mice. After 3 days vaccination, we could detect increased percentages of iNKT cells in the spleen of C57BL/6 mice vaccinated with PyrC-αGC (~12%) and NU-αGC (~6%), compared to mRNA Galsomes containing αGC (~3%), while a lower proliferation was observed for OCH (~1.8%) (FIG. 18A). Despite the distinct iNKT cell activities, all mRNA Galsomes were capable of inducing a strong proliferation of OVA-specific CD8⁺ T cells (>3%; measured after 7 days) (FIG. 18B). It should be noted that the same particles without any glycolipid adjuvant hardly result in OVA-specific CD8⁺ T cells. Subsequently, we evaluated to what extent the incorporation of different α-GalCer analogs would affect PD-1 expression on iNKT cells. Previous studies have demonstrated that there is an 'activation threshold' for iNKT anergy [28, 30]. As shown in FIG. 18C, we observed a significant lower expression of PD-1 by iNKT cells after treatment with OCH mRNA Galsomes.

Figure 18:
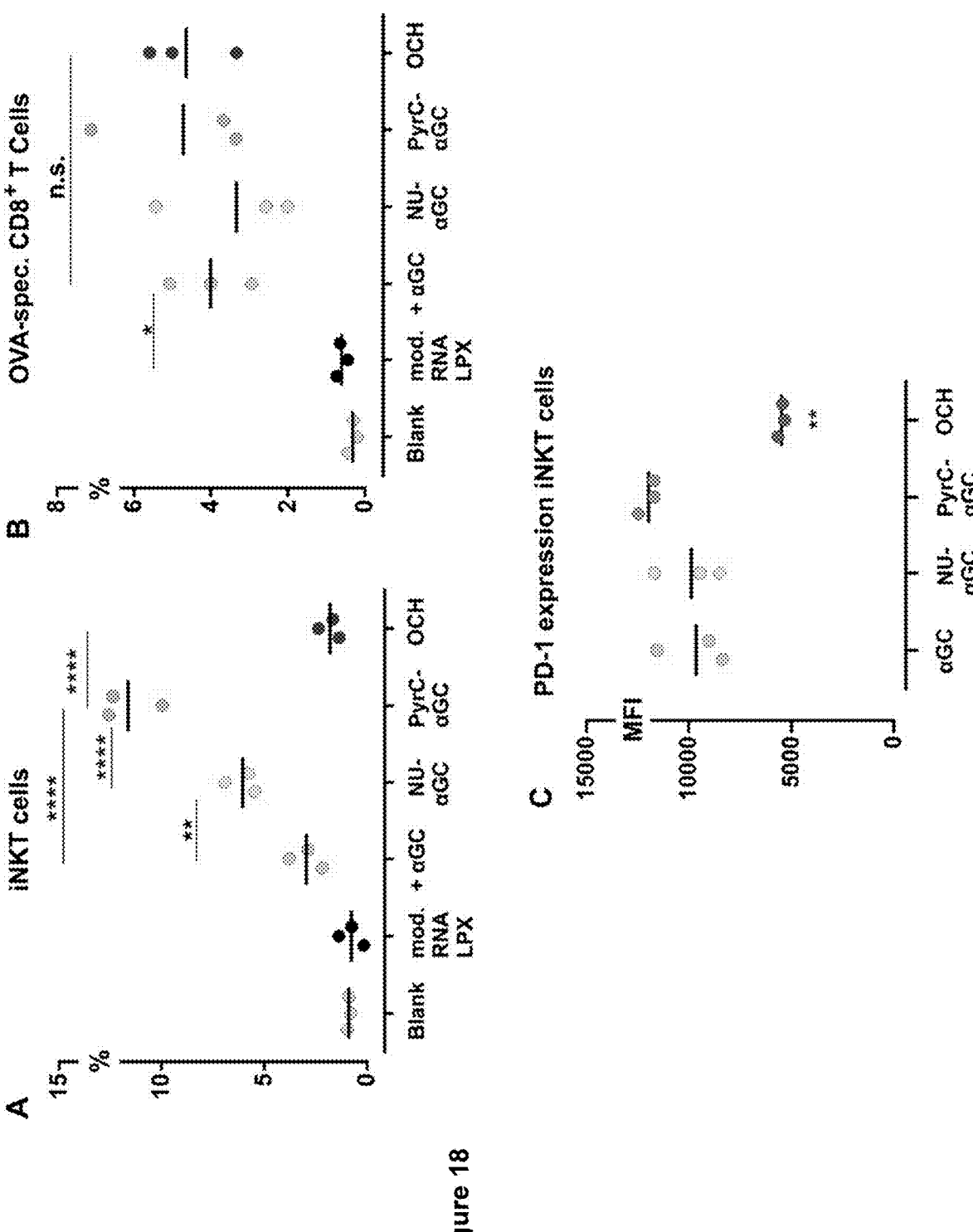
FIG. 18. Proliferation of iNKT cells and antigen-specific CTLs after mRNA Galsome vaccination with αGC analogs. (A) Spleens of C57BL/6 mice were analyzed for the presence of iNKT cells at 3 days after vaccination with mRNA Galsomes containing αGC or different αGC analogs (i.e. NU-αGC, PyrC-αGC or OCH). (B) Using a SIINFEKL-H2Kb tetramer staining, OVA-specific CD8$^+$ T cells were identified in the spleens of vaccinated mice (day 7). (C) PD-1 expression on iNKT cells. Statistical analysis compared to αGC was performed by one-way ANOVA followed by Tukey's post hoc test. (, $p<0.01$, *, $p<0.001$; ****, $p<0.0001$, n=3).
Figure 19:
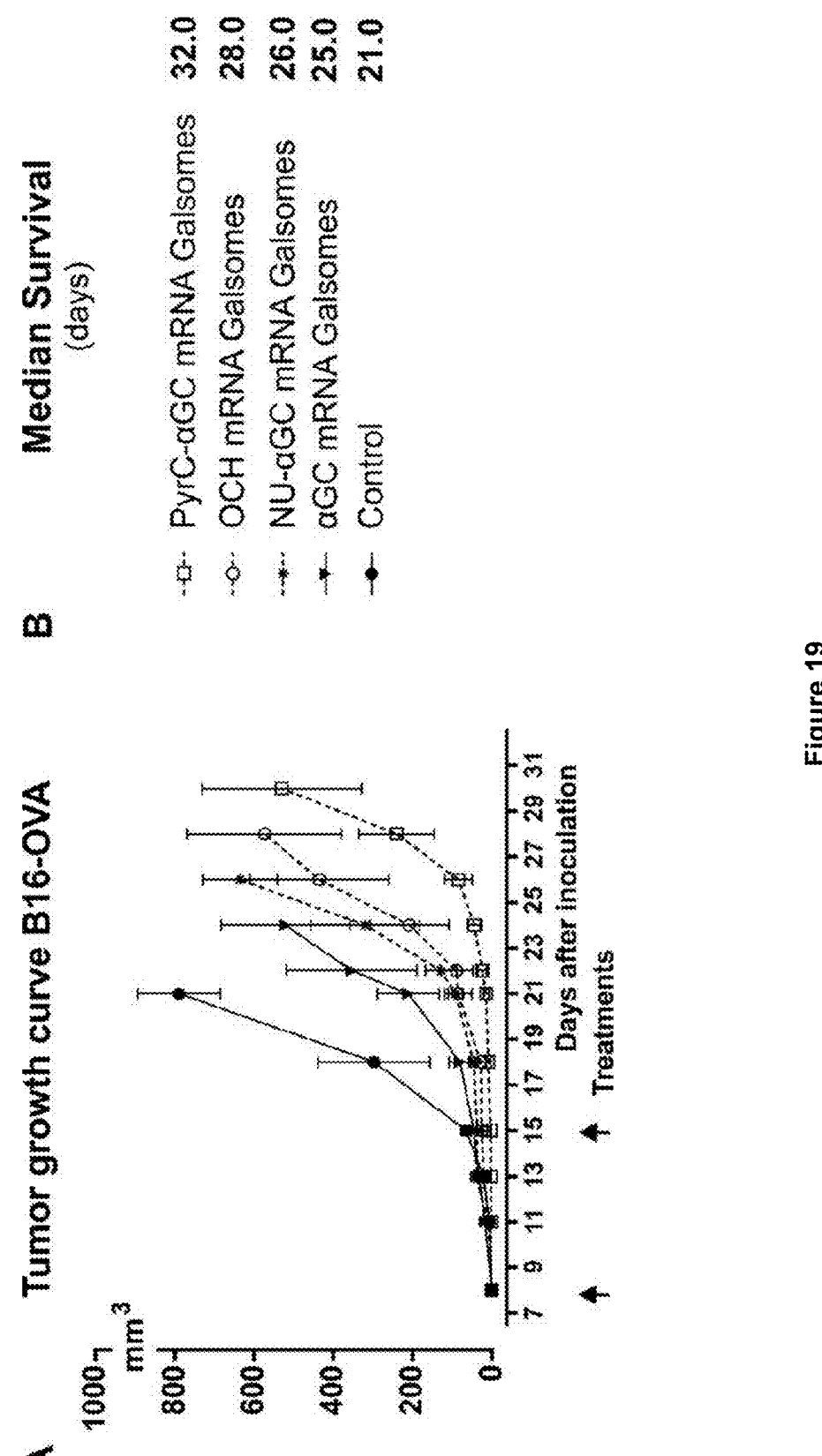
FIG. 19. Therapeutic vaccination in B16-OVA melanoma model with mRNA Galsomes containing either classic αGC or αGC analogs. Mice were subcutaneously inoculated with B16-OVA cells ($3 \times 10^5$ cells). B16-OVA-bearing mice were vaccinated on day 8 and received a boost vaccination on day 15. (A) Graph show tumor growth curves (until median survival time-point) and (B) respective median survival days for an untreated control group (negative control) and for mice treated with OVA mRNA Galsomes containing αGC or αGC analogs (i.e. NU-α-GC, PyrC-α-GC or OCH) (n=5-6).

Next, the therapeutic potential of mRNA Galsomes packaged with α-GalCer or these analogs was compared in the herein described B16-OVA melanoma model. B16-OVA bearing mice received a first vaccination on day 8 and a boost vaccination on day 15. FIG. 19 shows that mice vaccinated with mRNA Galsomes containing the α-GalCer analogs resulted in superior antitumor effects over particles formulated with classic α-GalCer. Both PyrC- and OCH analogs had the most pronounced impact on the tumor growth, demonstrated by an improved median survival of 32 days and 28 days, respectively, compared to 26 days for NU-α-GalCer and 25 days for α-GalCer, and 21 days for untreated animals. In case of the PyrC analogue, this can potentially be explained by the enhanced capacity of this analogue to stimulate iNKT cells (FIG. 18). In contrast, the superior antitumor effects of OCH might be explained by a reduced iNKT cell stimulation, hence resulting in lower PD-1 expression levels on iNKT cells after a single vaccination (FIG. 18C). By limiting the initial iNKT cell anergy, a second vaccination might have superior effects for the OCH analogue compared to the other α-GalCer variants, especially for establishing a continuous CTL response. Based on these results, the use of these α-GC analogs is found to be an extra appealing parameter that can modulate the efficacy and (potentially safety) of the mRNA Galsome formulation.

10. Co-Delivery of Nucleoside-Modified mRNA and α-GalCer Using an Alternative Lipid Nanoparticle System Composed With the Ionizable Lipid MC3.

Lipid nanoparticles composed with ionizable cationic lipids, and other "helper" lipids, such as a phospholipid, cholesterol and a poly(ethylene glycol) (PEG) lipid, are considered to be the most clinically advanced technology for RNA therapeutics. As outstanding example, the short interfering (si) RNA therapeutic Onpattro (patisiran) for the treatment of hereditary transthyretin-mediated amyloidosis, utilizing such ionizable LNP technology recently received as the first of its kind approval by the FDA and EMA. Moreover, these LNPs composed with a ionizable cationic lipid have also become the "gold standard" lipid formulation for the delivery of mRNA vaccines. We evaluated whether such lipid formulation, in particular with the ionizable lipid MC3, could also be used for the co-delivery of mRNA and α-GalCer as iNKT agonist.

Figure 20:
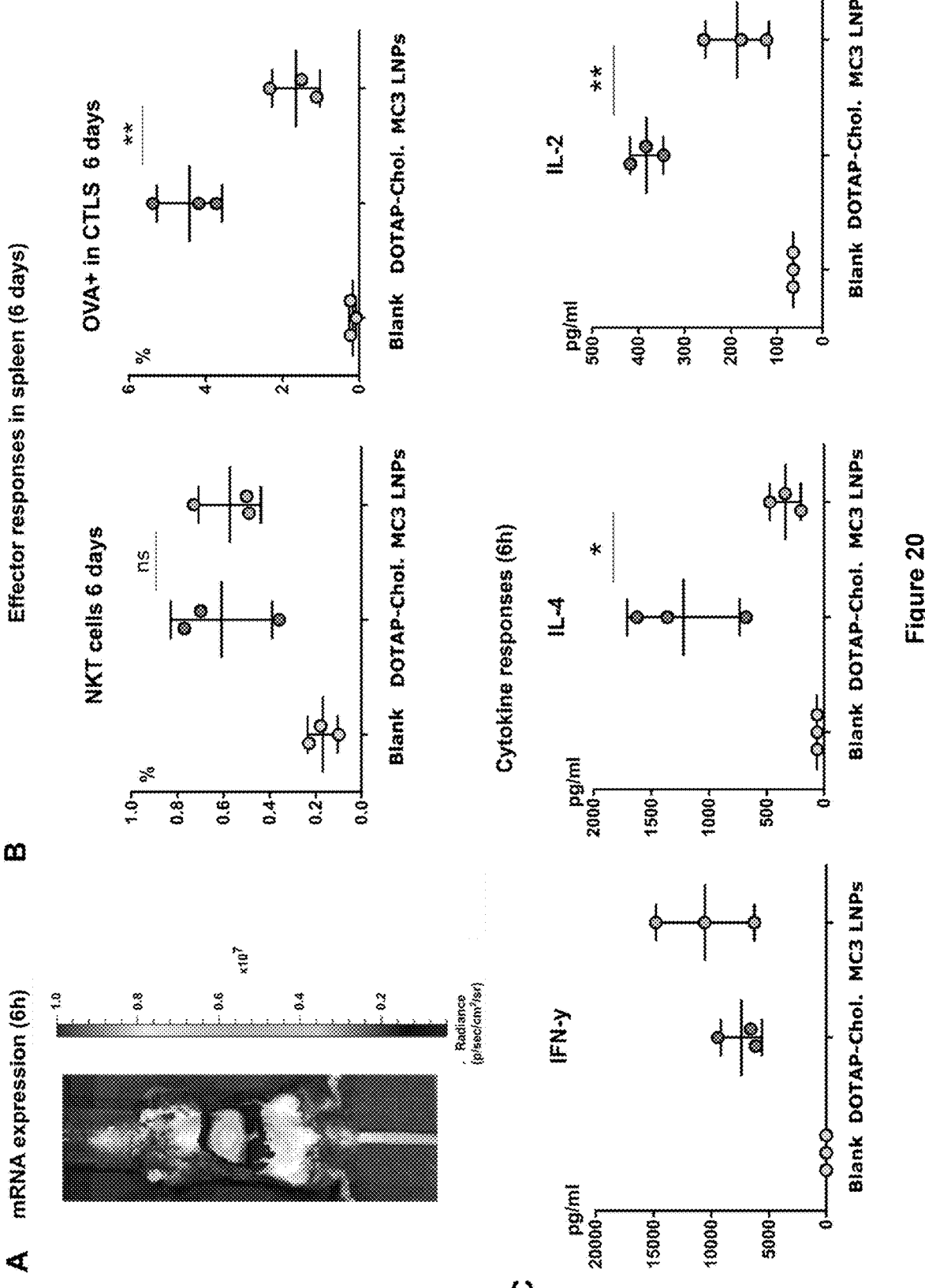
FIG. 20. Expression and immunogenicity from mRNA Galsomes composed with an "ionizable" lipid formulation (i.e. Dlin-MC3-DMA/DSPC/cholesterol/PEG-DMG). C57BL/6 mice were administered with MC3 mRNA Galsomes co-formulated with fLuc mRNA and tOVAI80 mRNA, and translation activity and immune effects were compared to the previously described DOTAP/cholesterol mRNA Galsomes. (A) Representative bioluminescence image of fLuc mRNA expression in mice 6h after administration of MC3 mRNA Galsomes. (B) Splenic percentages of iNKT cells and OVA-specific CTLs measured 6 days after vaccination with DOTAP-versus MC3 mRNA Galsomes. (C) Serum samples were collected at 6h post-injection and screened for the release of inflammatory cytokines.

To evaluate both the transfection efficiency and immunogenicity from MC3 LNPs adjuvanted with α-GalCer in the same animal, fLuc mRNA and tOVAI80 mRNA was co-formulated in a single nanoparticle. First of all, the systemic delivery of MC3 LNPs could achieve much higher whole body luciferase expression levels compared to mRNA Galsomes composed with DOTAP and cholesterol (FIG. 20A). Similar to previous reports, a remarkable high and selective mRNA expression was detected in the liver [33].

Importantly, an increased percentage of iNKT cells in the spleen is observed with cell numbers similar to the immunization with DOTAP mRNA Galsomes (FIG. 20B). Moreover, the MC3 mRNA Galsomes were also capable to induce OVA-specific CTLs measured in the spleen (1.65±0.62%), although to a lower extent than the DOTAP mRNA Galsomes (4.42±0.85%). In addition, early after immunization, Th1 and Th2 cytokine responses associated with iNKT cell stimulation could be detected in animals treated with MC3 mRNA Galsomes. Only a slight pattern shift in the cytokine polarization was observed with similar or higher cytokine levels of IFN-γ, TNF-α and IL-6, but lower levels of IL-4 and IL-2 (FIG. 20C). These differences might be linked to other organ distribution profiles of both the particles after systemic administration, stimulating other NKT cell subsets present in these nanoparticle-targeted organs.

In conclusion, these results show that LNPs using alternative cationic lipids can be used as carrier for the co-delivery of nucleoside-modified mRNA and α-GalCer, resulting in the stimulation of iNKT cells and the induction of enhanced antigen-specific T cell responses.

REFERENCES

[1] U. Sahin, K. Kariko, O. Tureci, Nature reviews. Drug discovery, 13 (2014), pp. 759-780.

[2] L. M. Kranz, M. Diken, H. Haas, S. Kreiter, C. Loquai, K. C. Reuter, M. Meng, D. Fritz, F. Vascotto, H. Hefesha, C. Grunwitz, M. Vormehr, Y. Husemann, A. Selmi, A. N. Kuhn, J. Buck, E. Derhovanessian, R. Rae, S. Attig, J. Diekmann, R. A. Jabulowsky, S. Heesch, J. Hassel, P. Langguth, S. Grabbe, C. Huber, O. Tureci, U. Sahin, Nature, 534 (2016), pp. 396-401.

[3] M. A. Oberli, A. M. Reichmuth, J. R. Dorkin, M. J. Mitchell, O. S. Fenton, A. Jaklenec, D. G. Anderson, R. Langer, D. Blankschtein, Nano letters, 17 (2017), pp. 1326-1335.

[4] B. R. Anderson, H. Muramatsu, S. R. Nallagatla, P. C. Bevilacqua, L. H. Sansing, D. Weissman, K. Karikó, Nucleic acids research, 38 (2010), pp. 5884-5892.

[5] O. Andries, S. Mc Cafferty, S. C. De Smedt, R. Weiss, N. N. Sanders, T. Kitada, J Control Release, 217 (2015), pp. 337-344.

[6] K. Kariko, M. Buckstein, H. Ni, D. Weissman, Immunity, 23 (2005), pp. 165-175.

[7] K. Kariko, H. Muramatsu, F. A. Welsh, J. Ludwig, H. Kato, S. Akira, D. Weissman, Molecular therapy: the journal of the American Society of Gene Therapy, 16 (2008), pp. 1833-1840.

[8] N. Pardi, M. J. Hogan, F. W. Porter, D. Weissman, Nature reviews. Drug discovery, 17 (2018), pp. 261-279.

[9] C. Iavarone, T. O'Hagan D, D. Yu, N. F. Delahaye, J. B. Ulmer, Expert Rev Vaccines, 16 (2017), pp. 871-881.

[10] F. Liang, G. Lindgren, A. Lin, E. A. Thompson, S. Ols, J. Rohss, S. John, K. Hassett, O. Yuzhakov, K. Bahl, L. A. Brito, H. Salter, G. Ciaramella, K. Lore, Molecular therapy: the journal of the American Society of Gene Therapy, 25 (2017), pp. 2635-2647.

[11] T. Pepini, A.-M. Pulichino, T. Carsillo, A. L. Carlson, F. Sari-Sarraf, K. Ramsauer, J. C. Debasitis, G. Maruggi, G. R. Otten, A. J. Geall, D. Yu, J. B. Ulmer, C. Iavarone, The Journal of Immunology, (2017).

[12] A. De Beuckelaer, C. Pollard, S. Van Lint, K. Roose, L. Van Hoecke, T. Naessens, V. K. Udhayakumar, M. Smet, N. Sanders, S. Lienenklaus, X. Saelens, S. Weiss, G. Vanham, J. Grooten, S. De Koker, Molecular therapy: the journal of the American Society of Gene Therapy, 24 (2016), pp. 2012-2020.

[13] J. Crouse, U. Kalinke, A. Oxenius, Nature reviews. Immunology, 15 (2015), pp. 231-242.

[14] A. De Beuckelaer, J. Grooten, S. De Koker, Trends in molecular medicine, 23 (2017), pp. 216-226.

[15] E. Jonasch, F. G. Haluska, The oncologist, 6 (2001), pp. 34-55.

[16] A. N. Theofilopoulos, R. Baccala, B. Beutler, D. H. Kono, Annual review of immunology, 23 (2005), pp. 307-336.

[17] N. Pardi, M. J. Hogan, M. S. Naradikian, K. Parkhouse, D. W. Cain, L. Jones, M. A. Moody, H. P. Verkerke, A. Myles, E. Willis, C. C. LaBranche, D. C. Montefiori, J. L. Lobby, K. O. Saunders, H. X. Liao, B. T. Korber, L. L. Sutherland, R. M. Scearce, P. T. Hraber, I. Tombacz, H. Muramatsu, H. Ni, D. A. Balikov, C. Li, B. L. Mui, Y. K.

Tam, F. Krammer, K. Kariko, P. Polacino, L. C. Eisenlohr, T. D. Madden, M. J. Hope, M. G. Lewis, K. K. Lee, S. L. Hu, S. E. Hensley, M. P. Cancro, B. F. Haynes, D. Weissman, The Journal of experimental medicine, 215 (2018), pp. 1571-1588.

[18] R. Verbeke, I. Lentacker, L. Wayteck, K. Breckpot, M. Van Bockstal, B. Descamps, C. Vanhove, S. C. De Smedt, H. Dewitte, J Control Release, 266 (2017), pp. 287-300.

[19] M. Diken, S. Kreiter, A. Selmi, C. M. Britten, C. Huber, O. Tureci, U. Sahin, Gene Ther, 18 (2011), pp. 702-708.

[20] K. G. Anderson, I. M. Stromnes, P. D. Greenberg, Cancer Cell, 31 (2017), pp. 311-325.

[21] A. Garcia-Diaz, D. S. Shin, B. H. Moreno, J. Saco, H. Escuin-Ordinas, G. A. Rodriguez, J. M. Zaretsky, L. Sun, W. Hugo, X. Wang, G. Parisi, C. P. Saus, D. Y. Torrejon, T. G. Graeber, B. Comin-Anduix, S. Hu-Lieskovan, R. Damoiseaux, R. S. Lo, A. Ribas, Cell reports, 19 (2017), pp. 1189-1201.

[22] C. Sun, R. Mezzadra, T. N. Schumacher, Immunity, 48 (2018), pp. 434-452.

[23] V. R. Juneja, K. A. McGuire, R. T. Manguso, M. W. LaFleur, N. Collins, W. N. Haining, G. J. Freeman, A. H. Sharpe, The Journal of experimental medicine, 214 (2017), pp. 895-904.

[24] S. Van Meirvenne, L. Straetman, C. Heirman, M. Dullaers, C. De Greef, V. Van Tendeloo, K. Thielemans, Cancer gene therapy, 9 (2002), pp. 787-797.

[25] K. Braeckmans, K. Buyens, W. Bouquet, C. Vervaet, P. Joye, F. De Vos, L. Plawinski, L. Doeuvre, E. Angles-Cano, N. N. Sanders, J. Demeester, S. C. De Smedt, Nano letters, 10 (2010), pp. 4435-4442.

[26] S. Fujii, K. Shimizu, C. Smith, L. Bonifaz, R. M. Steinman, The Journal of experimental medicine, 198 (2003), pp. 267-279.

[27] J. Devoldere, H. Dewitte, S. C. De Smedt, K. Remaut, Drug discovery today, (2015).

[28] V. V. Parekh, S. Lalani, S. Kim, R. Halder, M. Azuma, H. Yagita, V. Kumar, L. Wu, L. Van Kaer, J Immunol, 182 (2009), pp. 2816-2826.

[29] J. Wang, L. Cheng, Z. Wondimu, M. Swain, P. Santamaria, Y. Yang, The Journal of Immunology, 182 (2009), pp. 6644-6647.

[30] G. Wingender, A. M. Birkholz, D. Sag, E. Farber, S. Chitale, A. R. Howell, M. Kronenberg, J Immunol, 195 (2015), pp. 3838-3848.

[31] Kulkarni J A, et al. ACS Nano. 2018 May 22; 12(5): 4787-4795.

[32] Kulkarni J A, Tam Y Y C, Chen S, Tam Y K, Zaifman J, Cullis P R, Biswas S. Nanoscale. 2017 Sep. 21; 9(36): 13600-13609.

[33] Akinc A, et al. Mol Ther. 2010 July; 18(7):1357-64.

[34] Matthew B. Bloom et al. The Journal of Experimental Medicine • Volume 185, Number 3, Feb. 3, 1997 453-459.

The invention claimed is:

1. A nanoparticle comprising nucleoside-modified mRNA, a lipid component comprising a cationic lipid and cholesterol-based lipid or analog thereof, and an α-galactosylceramide (α-GalCer) compound, wherein the α-GalCer compound is incorporated is the lipid component of the nanoparticle.

2. The nanoparticle according to claim 1, wherein the cationic lipid is an ionizable cationic lipid.

3. The nanoparticle according to claim 1, wherein the cationic lipid is selected from the group consisting of: 1,2-Dioleoyl-3-Trimethylammonium-Propane (DOTAP), N-[1-(2,3-dioleyloxy)propyl]-N,N,N-trimethylammonium chloride (DOTMA), 5-carboxyspermylglycinedioctadecylamide (DOGS), 2,3-dioleyloxy-N-[2(spermine-carboxamido)ethyl]-N,N-dimethyl-l-propanaminium (DOSPA), 1,2-Dioleoyl-3-Dimethylammonium-Propane (DODAP), 1,2-distearyloxy-N,N-dimethyl-3-aminopropane (DSDMA), 1,2-dioleyloxy-N,N-dimethyl-3-aminopropane (DODMA), 1,2-dilinoleyloxy-N,N-dimethyl-3-aminopropane (DLinDMA), heptatriaconta-6,9,28,31-tetraen19-yl 4-(dimethylamino)butanoate (DLin-MC3-DMA), 2,2-dilinoleyl-4-(2-dimethylaminoethyl)-[1,3]-dioxolane (DLin-KC2-DMA), 1,2-dilinolenyloxy-N,N-dimethyl-3-aminopropane (DLenDMA), N-dioleyl-N,N-dimethylammonium chloride (DODAC), N,N-distearyl-N,N-dimethylammonium bromide (DDAB), N-(1,2-dimyristyloxyprop-3-yl)-N, N-dimethyl-N-hydroxyethyl ammonium bromide (DMRIE), 3-dimethylamino-2-(cholest-5-en-3-beta-oxybutan-4-oxy)-1-(cis, cis-9,12-octadecadienoxy)propane (CLinDMA), 2-[5'-(cholest-5-en-3-beta-oxy)-3'-oxapentoxy)-3-dimethyl-1-(cis,cis-9',1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 2,3-Dilinoleoyloxy-N,N-dimethylpropylamine (DLinDAP), 1,2-N,N'-Dilinoleylcarbamyl-3-dimethylaminopropane (DLincarbDAP), 1,2-Dilinoleoylcarbamyl-3-dimethylaminopropane (DLinCDAP), 2,2-dilinoleyl-4-dimethylaminoethyl-[1,3]-dioxolane (DLin-K-XTC2-DMA), and C12-200.

4. The nanoparticle according to claim 1, wherein the mRNA encodes an antigen or polypeptide.

5. The nanoparticle according to claim 1, wherein the nucleoside-modified mRNA comprises a modified nucleotide selected from pseudouridine (Ψ), N1-methylpseudouridine (m1Ψ), and/or 5-methylcytidine (5meC).

6. The nanoparticle according to claim 1, wherein the cholesterol-based lipid or analog thereof is selected from the group consisting of cholesterol, DC-Cholesterol, 3beta-[N—(N',N'-dimethylaminoethane)-carbamoyl] cholesterol, 1,4-bis(3-N-oleylamino-propyl)piperazine, imidazole cholesterol ester lipid (ICE), fecosterol, sitosterol, ergosterol, campersterol, stigmasterol, brassicasterol, tomatidine, ursolic acid, and alpha-tocopherol.

7. The nanoparticle according to claim 1, wherein a concentration of the α-GalCer compound in the nanoparticle is between and about 0.0015 mol % and about 1 mol % of the total lipid amount.

8. The nanoparticle according to claim 1, wherein the α-GalCer compound is α-Galactosylceramide, or an analog thereof, wherein said analog is a glycosphingolipid comprising a galactose carbohydrate attached by an α-linkage to a ceramide lipid that has an acyl and sphingosine chains of variable lengths.

9. The nanoparticle according to claim 8, wherein the α-GalCer compound is selected from the group consisting of: HS44, BbGL-II, threitolceramide, ABX196, PBS-25, PBS-57, α-C-GalCer, OCH, Naphtylureum-α-GalCer or NU-α-GalCer, Alpha-GalCer-6"-(4-pyridyl)carbamate or PyrC-α-GalCer, (3S,4S,5R)-1-(6"-O-(4-pyridinylcarbamoyl)-α-C-D-galacto-pyranosyl)-3-hexacosylamino-nonadecane-4,5-diol, (3S,4S,5R)-1-(6"-O-(4-pyridinylcarbamoyl)-α-C-D-galacto-pyranosyl)-3-hexacosylamino-l-nonadecene-4,5-diol, (3S,4S,5R)-1-(6"-naphtureido-6"-deoxy-α-C-D-galacto-pyranosyl)-3-hexacosylamino-nonadecane-4,5-diol, (3S,4S,5R)-1-(6"-naphtureido-6"-deoxy-α-C-D-galacto-pyranosyl)-3-hexacosylamino-1-nonadecene-4,5-diol, α-1C-GalCer, and 7DW8-5.

10. A pharmaceutical composition comprising the nanoparticle according to claim 1, and a pharmaceutically acceptable excipient or diluent.

11. The nanoparticle according to claim 1, wherein the nucleoside-modified mRNA comprises a stem loop, a chain terminating nucleoside, a polyA sequence, a polyadenylation signal, a 5' cap structure, or combinations thereof.

\* \* \* \* \*